United States Patent

Baudoin et al.

Patent Number: 5,861,529
Date of Patent: Jan. 19, 1999

[54] FARNESYL TRANSFERASE INHIBITORS, THEIR PREPARATION AND THE PHARMACEUTICAL COMPOSITIONS WHICH CONTAIN THEM

[75] Inventors: Bernard Baudoin, Chaville, France; Christopher Burns, Rosemont, Pa.; Alain Commercon, Vitry-sur-Seine; Jean-Dominique Guitton, Paris, both of France

[73] Assignee: Rhone-Poulenc Rorer S.A., Antony, France

[21] Appl. No.: 750,819

[22] PCT Filed: Jun. 7, 1995

[86] PCT No.: PCT/FR95/00739

§ 371 Date: Jun. 18, 1997

§ 102(e) Date: Jun. 18, 1997

[87] PCT Pub. No.: WO95/34535

PCT Pub. Date: Dec. 21, 1995

[30] Foreign Application Priority Data

Jun. 10, 1994 [FR] France .................................. 94 07116

[51] Int. Cl.⁶ .......................... C07C 32/00; A01N 37/12
[52] U.S. Cl. ........................... 560/9; 562/426; 514/534
[58] Field of Search .............................. 560/9; 562/426; 514/534

[56] References Cited

FOREIGN PATENT DOCUMENTS 0 461 869 A3  12/1991  European Pat. Off. .
WO 94/00419   1/1994   WIPO .
WO 94/09766   5/1994   WIPO .

OTHER PUBLICATIONS

S. Graham et al., "Pseudopeptide Inhibitors of Ras Farnesyl–Protein Transferase", J. Med. Chem., 37(6):725–732 (1994).

Primary Examiner—Paul J. Killos
Attorney, Agent, or Firm—Finnegan, Henderson, Farabow, Garrett & Dunner, L.L.P.

[57] ABSTRACT

This invention relates to transferase inhibitors of the formula (I), their preparation, and pharmaceutical compositions containing them.

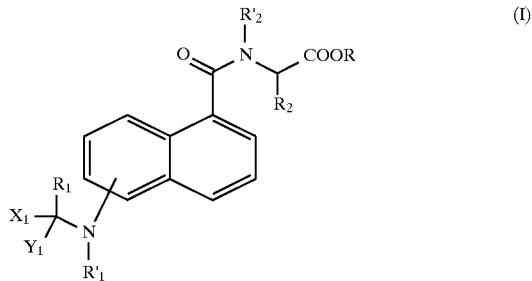

In formula (I), $R_1$ is $Y-S-A_1-$ (Y is a hydrogen atom, an amino acid residue, a fatty acid residue, an alkyl radical, an alkoxycarbonyl radical, or an $R_4-S-$ radical in which $R_4$ is an alkyl radical containing 1 to 4 carbon atoms optionally substituted by a phenyl radical or a radical of the formula (II)

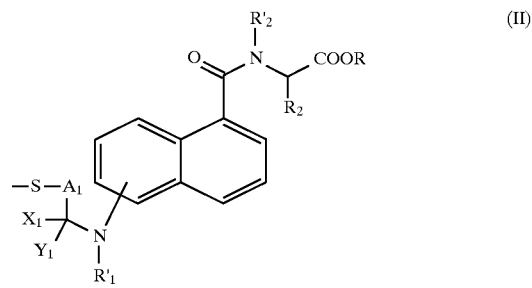

in which $A_1$ is an alkylene radical containing 1 to 4 carbon atoms optionally substituted at the position a in the grouping $>C(X_1)(Y_1)$ with an amino, alkylamino, dialkylamino, alkanoylamino, or alkoxycarbonylamino radical); $X_1$ and $Y_1$ are each a hydrogen atom or form, together with the carbon atom to which they are connected, a $>C=O$ grouping; $R'_1$ is hydrogen or methyl; $R_2$ is an alkyl, alkenyl or an alkynyl radical containing 1 to 6 carbon atoms optionally substituted by a hydroxyl, alkoxy, mercapto, alkylthio, alkylsulphinyl, or alkylsulphonyl, wherein when $R_2$ is an alkyl radical substituted by a hydroxyl radical, $R_2$ can form a lactone with the carboxyl radical at the α position; $R'_2$ is hydrogen or methyl; and R is a hydrogen atom or an optionally substituted alkyl radical or an optionally substituted phenyl radical; and the radical

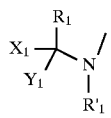

is in position 5 or 6 of the naphthyl ring. These compounds have anti-cancer properties.

5 Claims, No Drawings

FARNESYL TRANSFERASE INHIBITORS, THEIR PREPARATION AND THE PHARMACEUTICAL COMPOSITIONS WHICH CONTAIN THEM

The present invention relates to new farnesyl transferase inhibitors of general formula:

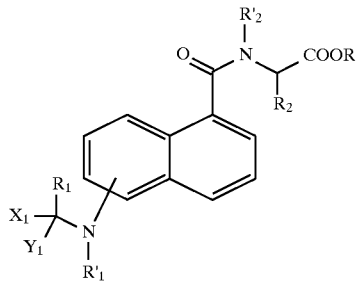

optionally to their salts, to their preparation and to pharmaceutical compositions which contain them.

The inhibition of farnesyl transferase, and consequently of the farnesylation of the Ras protein, blocks the capacity of the mutated Ras protein to transform normal cells into cancerous cells.

The C-terminal sequence of the Ras gene contains the unit "CAAX" or "Cys-Aaa$_1$-Aaa$_2$-Xaa", in which Aaa represents an aliphatic amino acid and Xaa represents any amino acid.

It is known that tetrapeptides with a CAAX sequence can inhibit the farnesylation of the Ras protein. For example, peptide inhibitors of farnesyl transferase, Cys-Aaa$_1$-Aaa$_2$-Xaa, which are especially represented by the peptides Cys-Val-Leu-Ser, Cys-Val-Ile-Met and Cys-Val-Val-Met which manifest their inhibitory activity at concentrations in the region of $10^{-6}$M or of $10^{-7}$M, have been described in PCT Application WO 91/16340 and in Application EP 0,461,869 hereby incorporated by reference.

It has now been found, and this forms the subject of the present invention, that the peptides of general formula (I) manifest their inhibitory activity (IC$_{50}$) at concentrations of the order of $10^{-8}$ or of $10^{-9}$M.

In the general formula (I), R$_1$ represents a radical of general formula Y—S—A$_1$— in which Y represents a hydrogen atom or an amino acid residue or a fatty acid residue or an alkyl or alkoxycarbonyl radical or an R$_4$—S— radical in which R$_4$ represents an alkyl radical containing 1 to 4 carbon atoms, optionally substituted by a phenyl radical, or a radical of general formula:

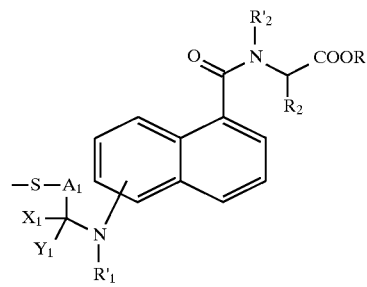

in which A$_1$, X$_1$, Y$_1$, R'$_1$, R$_2$, R'$_2$ and R are defined as below, and A$_1$ represents a straight or branched alkylene radical containing 1 to 4 carbon atoms, optionally substituted at the position a to the >C(X$_1$) (Y$_1$) group by an amino radical, an alkylamino radical containing 1 to 6 straight- or branched-chain carbon atoms, a dialkyl-amino radical in which each alkyl part contains 1 to 6 straight- or branched-chain carbon atoms, an alkanoyl-amino radical containing 1 to 6 straight- or branched-chain carbon atoms or an alkoxycarbonylamino radical in which the alkyl part contains 1 to 6 straight- or branched-chain carbon atoms, X$_1$ and Y$_1$ each represent a hydrogen atom or form, together with the carbon atom to which they are bonded, a >C=O group, R'$_1$ represents a hydrogen atom or a methyl radical, R$_2$ represents a straight or branched alkyl, alkenyl or alkynyl radical containing 1 to 6 carbon atoms, optionally substituted by a hydroxyl radical, an alkoxy radical containing 1 to 4 carbon atoms, a mercapto radical, an alkylthio radical containing 1 to 4 carbon atoms, an alkylsulphinyl radical containing 1 to 4 carbon atoms or an alkylsulphonyl radical containing 1 to 4 carbon atoms, it being understood that, when R$_2$ represents an alkyl radical substituted by a hydroxyl radical, R$_2$ can form a lactone with the carboxyl radical at the α position, R'$_2$ represents a hydrogen atom or a methyl radical, and R represents a hydrogen atom or an alkyl radical containing 1 to 6 carbon atoms, optionally substituted by an alkoxy radical containing 1 to 4 carbon atoms, an alkylthio radical containing 1 to 4 carbon atoms, an alkylsulphinyl radical containing 1 to 4 carbon atoms, an alkylsulphonyl radical containing 1 to 4 carbon atoms, a phenyl radical, a phenoxy radical, a phenylthio radical, a phenylsulphinyl radical, a phenylsulphonyl radical, an alkylamino radical containing 1 to 4 carbon atoms or a dialkylamino radical in which each alkyl part contains 1 to 4 carbon atoms, or a phenyl radical, optionally substituted by one or a number of atoms or radicals chosen from halogen atoms and alkyl, alkyloxy, alkylthio or alkanoyl radicals, it being understood that the radical

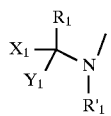

is in the 5- or 6-position of the naphthyl ring.

More particularly, R$_1$ represents a radical of formula Y—S—A$_1$— in which Y represents a hydrogen atom or a lysine residue or a fatty acid residue containing up to 20 carbon atoms and A$_1$ represents an ethylene or propylene radical optionally substituted by an amino radical or an alkylamino radical containing 1 to 4 carbon atoms, X$_1$ and Y$_1$ each represent a hydrogen atom or form, together with the carbon atom to which they are bonded, a >C=O group, R'$_1$ represents a hydrogen atom or a methyl radical, R$_2$ represents an alkyl radical containing 1 to 4 carbon atoms, optionally substituted by a hydroxyl, methoxy, mercapto, methylthio, methylsulphinyl or methylsulphonyl radical, R'$_2$ represents a hydrogen atom or a methyl radical, and R represents a hydrogen atom or an alkyl radical containing 1 to 4 carbon atoms, optionally substituted by an alkoxy radical, or a phenyl radical.

More particularly still, R$_1$ represents a radical of formula Y—S—A$_1$— in which Y represents a hydrogen atom and A$_1$ represents an ethylene or propylene radical optionally substituted by an amino radical, X$_1$ and Y$_1$ each represent a hydrogen atom or form, together with the carbon atom to which they are bonded, a >C=O group, R'$_1$ represents a hydrogen atom, R$_2$ represents a methyl, ethyl, propyl or butyl radical optionally substituted by a hydroxyl, methoxy, mercapto or methylthio radical, R'$_2$ represents a hydrogen atom, and R represents a hydrogen atom or an alkyl radical containing 1 to 4 carbon atoms.

The products of general formula (I) in which R$_1$ represents a 2-mercaptoethyl or 1-amino-2-mercaptoethyl radical, X$_1$ and Y$_1$ each represent a hydrogen atom or form, together with the carbon atom to which they are bonded, a >C=O group, $R'_1$ represents a hydrogen atom, $R_2$ represents an n-butyl or 2-(methylthio)ethyl radical and $R'_2$ represents a hydrogen atom, and R represents a hydrogen atom or a methyl radical are very particularly advantageous.

The present invention also relates to the stereoisomeric forms of the products of general formula (I). The amino acid residues represented by $R_1 C(X_1) (Y_1) (NR'_1)$ and $R_3CH (NR'_3)CO$—OH preferably have the configuration of the natural amino acids.

The present invention also relates to the inorganic or organic salts of the products of general formula (I).

The new products according to the invention can be prepared by the application of known methods derived from the methods used more particularly in peptide chemistry for chain assembly.

Generally, the products of general formula (I), in which $X_1$ and $Y_1$ form, together with the carbon atom to which they are bonded, a >C=O group, are obtained from 5-nitro- or 6-nitronaphthalene-1-carboxylic acid, with which is condensed an amino acid of general formula:

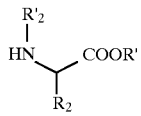
(III)

in which $R_2$ and $R'_2$ are defined as above and R' represents an alkyl radical containing 1 to 4 carbon atoms which is optionally substituted by a phenyl radical, preferably a tert-butyl radical, the reaction being carried out in the presence of a coupling agent, such as hydroxybenzotriazole and dicyclohexylcarbodiimide or N'-(3-dimethylaminopropyl)-N-ethylcarbodiimide hydrochloride, and of a base, such as triethylamine, in an organic solvent, such as dimethylformamide, in order to give a product of general formula:

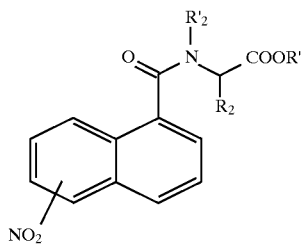
(IV)

in which $R_2$, $R'_2$ and R' are defined as above, which is reduced, preferably by means of stannous chloride or by hydrogen in the presence of a catalyst such as palladium, to a product of general formula:

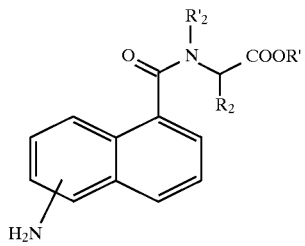
(V)

in which $R_2$, $R'_2$ and R' are defined as above, with which is condensed a product of formula:

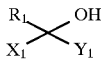
(VI)

in which $R_1$ is defined as above and $X_1$ and $Y_1$ form, together with the carbon atom to which they are bonded, a >C=O group, it being understood that the amino and mercapto functional groups carried by $R_1$ are optionally protected by appropriate protecting groups, such as a trityl radical for the mercapto functional group or a tert-butoxycarbonyl radical for the amino functional group, the reaction preferably being carried out in the presence of an alkyl haloformate (isobutyl chloroformate) and of an organic base (N-methylmorpholine) in an inert organic solvent (tetrahydrofuran), in order to obtain a product of general formula:

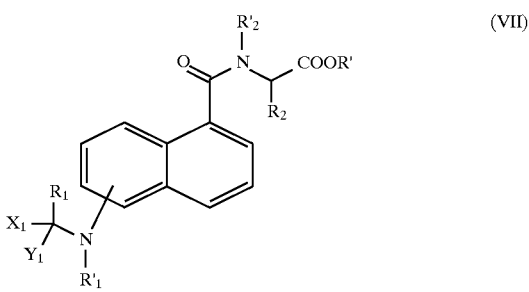
(VII)

in which the symbols $R_1$, $R'_1$, $X_1$, $Y_1$, $R_2$, $R'_2$ and $R_1$ are defined as above, the protective groups of which are replaced by hydrogen atoms, by means of trifluoroacetic acid in the presence of ethanedithiol or of triethylsilane, when the protective groups represent trityl, tert-butoxycarbonyl or tert-butyl radicals, in order to obtain a product of general formula (I) in which $X_1$ and $Y_1$ form, together with the carbon atom to which they are bonded, a >C=O group.

Generally, the products of general formula (I) in which the symbols $X_1$ and $Y_1$ each represent a hydrogen atom can be obtained by reaction of an aldehyde of general formula:

$R_1$—CHO (VIII)

in which $R_1$ is defined as above, it being understood that the amino and mercapto functional groups carried by $R_1$ are optionally protected by appropriate protecting groups, such as a trityl radical for the mercapto functional group or a tert-butoxycarbonyl radical for the amino functional group, with a product of general formula (V) in the presence of a reducing agent, such as sodium cyanoborohydride, sodium borohydride, sodium triacetoxyborohydride or hydrogen in the presence of a catalyst. Generally, the reaction is carried out in an organic solvent such as an alcohol, for instance methanol, optionally in combination with another organic solvent such as an ether, for instance tetrahydrofuran. It is particularly advantageous to carry out the reaction in anhydrous medium.

Condensation of the aldehyde with the amine having been carried out, the protecting groups are replaced by hydrogen atoms by application of the usual techniques. Thus, the Boc or trityl or tert-butyl protecting groups can be replaced by hydrogen atoms by means of trifluoroacetic acid in the presence of ethanedithiol or triethylsilane.

When, in the general formula (I), the $R_2$ symbol forms a lactone with the carboxyl functional group in the a position, treatment in basic medium of the corresponding product leads to the product of general formula (I) in which $R_2$ represents an alkyl radical substituted by a hydroxyl radical. Generally, opening of the lactone takes place as soon as the pH becomes greater than 7. It is particularly advantageous to carry out the reaction in the presence of an inorganic base (sodium hydroxide or potassium hydroxide) in aqueous/alcoholic medium, such as a water/methanol mixture.

The products of general formula (I) in which R represents a hydrogen atom can be obtained by saponification of a product of general formula (I) in which R represents an optionally substituted alkyl radical or or optionally substituted phenyl radical.

The products of general formula (I) in which R represents an optionally substituted alkyl radical or an optionally substituted phenyl radical as indicated above can be obtained by esterification of a product of general formula (I) in which R represents a hydrogen atom under the usual esterification conditions which do not affect the remainder of the molecule.

5-Nitro- or 6-nitronaphthalene-1-carboxylic acids can be prepared according to the process described by T. Nakayama et al., Chem. Pharm. Bull., 32, 3968 (1984) hereby incorporated by reference.

S-Triphenylmethyl-N-(tert-butoxycarbonyl)cysteinal can be prepared according to the process described in European Patent Application EP 0,618,221 hereby incorporated.

The products of general formula (I) can be purified according to the usual methods, such as chromatography.

The following examples illustrate the preparation of the products according to the invention.

EXAMPLE 1

5-Nitronaphthalene-1-carboxylic acid is prepared according to the method of T. Nakayama et al., Chem. Pharm. Bull., 32, 3968 (1984).

2 g of (L)-methionine methyl ester hydrochloride, 1.35 g of 1-hydroxybenzotriazole, 1.4 cm$^3$ of triethylamine and 2.06 g of dicyclohexylcarbodiimide are added to a solution of 2.17 g of 5-nitronaphthalene-1-carboxylic acid in 30 cm$^3$ of dichloromethane and 13 cm$^3$ of dimethylformamide. The reaction mixture is stirred for 20 hours at a temperature in the region of 20° C., then filtered on sintered glass, washed with twice 5 cm$^3$ of dimethylformamide and then concentrated to dryness under reduced pressure. The residue obtained is dissolved in 100 cm$^3$ of dichloromethane and washed with a 10% (w/v) aqueous sodium hydrogen carbonate solution, then with a 10% aqueous acetic acid solution and finally with a saturated aqueous sodium chloride solution. The organic phase is dried over magnesium sulphate, filtered and then concentrated to dryness under reduced pressure. 3.4 g of a brown solid are obtained, which solid is purified by chromatography on silica [eluent: dichloromethane/ethyl acetate (95/5 by volume)]. 2.6 g of the methyl ester of N-[(5-nitronaphthyl)-1-carbonyl]-L-methionine are thus obtained in the form of a solid, the characteristics of which are the following:

proton nuclear magnetic resonance spectrum (300 MHz, d6-(CD$_3$)$_2$SO, δ in ppm): from 2.00 to 2.25 (mt, 2 H, CH$_2$), 2.11 (s, 3 H, SCH$_3$), 2.65 (mt, 2 H, SCH$_2$), 3.77 (s, 3 H, OCH$_3$), 4.70 (mt, 1 H, CHN), 7.82 and 7.89 (2 t, J=8.5 Hz, 2 H, H at 3 and H at 7), 7.85 (d, J=8.5 Hz, 1 H, H at 2), 8.36 (d, J=8.5 Hz, 1 H, H at 4), 8.43 (d, J=8.5 Hz, 1 H, H at 8), 8.57 (d, J=8.5 Hz, 1 H, H at 6), 9.17 (d, J=7.5 Hz, 1 H, CONH).

3.39 g of tin(II) chloride dihydrate are added to a solution of 1.09 g of the methyl ester of N-[(5-nitronaphthyl)-1-carbonyl]-L-methionine in 23 cm$^3$ of ethyl acetate and 6 cm$^3$ of ethanol. The reaction mixture is stirred for 30 minutes at a temperature in the region of 70° C., poured onto ice and then brought to a pH in the region of 7–8 by addition of a 5% (w/v) aqueous sodium hydrogen carbonate solution. The mixture obtained is filtered on sintered glass covered with Celite. The organic phase is separated by settling and the aqueous phase is extracted 3 times with 50 cm$^3$ of ethyl acetate. The organic phases are combined, dried over magnesium sulphate, filtered and concentrated to dryness under reduced pressure. 0.9 g of methyl ester of N-[(5-aminonaphthyl)-1-carbonyl]-L-methionine is thus obtained in the form of an oil, the characteristics of which are the following:

proton nuclear magnetic resonance spectrum (200 MHz, d6-(CD$_3$)$_2$SO with addition of a few drops of d4-CD$_3$COOD, δ in ppm): from 1.95 to 2.25 (mt, 2 H, CH$_2$), 2.09 (s, 3 H, SCH$_3$), 2.62 (mt, 2 H, SCH$_2$), 3.71 (s, 3 H, OCH$_3$), 4.63 (mt, 1 H, CHCOO), 6.71 (d, J=8.5 Hz, 1 H, H at 6), from 7.15 to 7.60 (mt, 4 H, aromatic H), 8.18 (d, J=8.5 Hz, 1 H, H at 8), 8.84 (poorly-resolved d, J=7.5 Hz, 1 H, CONH).

0.35 cm$^3$ of isobutyl chloroformate and then a solution of 0.9 g of the methyl ester of N-[(5-aminonaphthyl)-1-carbonyl]-L-methionine in 20 cm$^3$ of tetrahydrofuran are added to a solution of 1.25 g of N-tert-butoxycarbonylamino-S-triphenylmethyl-L-cysteine and 0.3 cm$^3$ of N-methylmorpholine in 25 cm$^3$ of tetrahydrofuran, at a temperature in the region of −15° C. The reaction mixture is stirred for 2 days at a temperature in the region of 20° C. and then filtered and concentrated to dryness under reduced pressure. The residue obtained is dissolved in 50 cm$^3$ of ethyl acetate and washed with distilled water, then with a 0.5N aqueous sodium hydrogen carbonate solution, a 10% (w/v) aqueous citric acid solution and finally with distilled water. The organic phase is dried over magnesium sulphate, filtered and concentrated to dryness under reduced pressure. 2 g of a yellow foam are thus obtained, which foam is purified by chromatography on silica [eluent: dichloromethane/ethyl acetate (90/10 by volume)]. 1.5 g of the methyl ester of N-[5-(2(R)-tert-butoxycarbonylamino-3-(triphenylmethylthio)propionylamino)naphthyl-1-carbonyl]-L-methionine are obtained in the form of a solid, the characteristics of which are the following:

proton nuclear magnetic resonance spectrum (300 MHz, d6-(CD$_3$)$_2$SO, δ in ppm): 1.43 (s, 9 H, C(CH$_3$)$_3$), from 2.00 to 2.25 (mt, 4 H, CH$_2$ and CH$_2$SAr), 2.08 (s, 3 H, SCH$_3$), 2.60 (mt, 2 H, SCH$_2$), 3.74 (s, 3 H, OCH$_3$), 4.32 (mt, 1 H, NCH), 4.64 (mt, 1 H, CHCOO), from 7.20 to 7.80 (mt, 20 H, aromatic H and CONH), from 8.00 to 8.15 (mt, 2 H, H at 8 and H at 6), 9.02 (d, J=8 Hz, 1 H, CONH), 10.08 (s, 1 H, ArNH).

0.061 g of lithium hydroxide dihydrate is added to a solution of 0.45 g of the methyl ester of N-[5-(2(R)-tert-butoxycarbonylamino-3-(triphenylmethylthio)propionylamino)naphthyl-1-carbonyl]-L-methionine in 1 cm$^3$ of water and 10 cm$^3$ of tetrahydrofuran, at a temperature in the region of 5° C. The solution is stirred for 4 hours at a temperature in the region of 20° C. and then concentrated under reduced pressure. 0.47 g of N-[5-(2(R)-tert-butoxycarbonyl-amino-3-triphenylmethylthio)propionylamino)naphthyl-1-carbonyl]-L-methionine is obtained in the form of a foam.

2 cm$^3$ of trifluoroacetic acid are added, at a temperature in the region of 5° C., to a mixture of 0.44 g of N-[5-(2(R)-tert-butoxycarbonylamino-3-(triphenylmethylthio)propionylamino)naphthyl-1-carbonyl]-L-methionine in 2 cm$^3$ of water and 2 cm$^3$ of ethanedithiol. The reaction mixture is then stirred for 2 hours at a temperature in the region of 20° C. and then 20 cm$^3$ of trifluoroacetic acid are added dropwise. The reaction mixture is stirred for 2 hours and then filtered and concentrated under reduced pressure. The residue obtained is triturated twice with 30 cm³ of ethyl ether and then dried under reduced pressure. 0.23 g of the trifluoroacetate of N-[5-(2(R)-amino-3-mercaptopropionylamino)naphthyl-1-carbonyl]-L-methionine is thus obtained in the form of a white solid, the characteristics of which are the following:

proton nuclear magnetic resonance spectrum (200 MHz, d6-$(CD_3)_2SO$, δ in ppm): from 1.90 to 2.25 (mt, 2 H, $CH_2$), 2.10 (s, 3 H, $SCH_3$), 2.65 (mt, 2 H, $SCH_2$), 3.15 (d, J=7 Hz, 2 H, $SCH_2$), 4.28 (mt, 1 H, NCH), 4.61 (mt, 1 H, CHCOO), from 7.45 to 7.80 (mt, 4 H, aromatic H), from 8.10 to 8.30 (mt, 2 H, H at 8 and H at 6), 8.90 (d, J=8 Hz, 1 H, CONH), 10.20 (unresolved peak, 1 H, ArNHCO).

Elemental analysis: $C_{19}H_{23}N_3O_4S_2 \cdot 1.5CF_3CO_2H$: Calculated (%): C=45.78, H=4.33, N=7.45, S=11.37 Found (%): C=45.92, H=4.05, N=7.54, S=11.66.

EXAMPLE 2

By carrying out the process as in Example 1 for the preparation of the trifluoroacetate of N-[5-(2(R)-amino-3-mercaptopropionylamino)naphthyl-1-carbonyl]-L-methionine, but from 0.52 g of methyl ester of N-[5-(2(R)-tert-butoxycarbonylamino-3-(triphenylmethylthio)propionylamino)naphthyl-1-carbonyl]-L-methionine, 0.17 g of trifluoroacetate of the methyl ester of N-[5-(2(R)-amino-3-mercaptopropionylamino)naphthyl-1-carbonyl]-L-methionine is obtained, the characteristics of which are the following:

proton nuclear magnetic resonance spectrum (300 MHz, d6-$(CD_3)_2SO$, δ in ppm): 2.08 (mt, 2 H, $CH_2$), 2.10 (s, 3 H, $SCH_3$), 2.64 (mt, 2 H, $CH_2S$), 3.21 (d, J=6 Hz, 2 H, $SCH_2$), 3.78 (S, 3 H, $COOCH_3$), 4.39 (t, J=6 Hz, 1 H, CHN), 4.69 (mt, 1 H, CHCOO), from 7.60 to 7.80 (mt, 4 H, H2—H3—H6 and H7), 8.13 (d, J=8.5 Hz, 1 H, H8), 8.25 (dd, J=7.5 and 2.5 Hz, 1 H, H4), from 8.00 to 8.60 (unresolved peak, 2 H, $NH_2$), 9.05 (d, J=7.5 Hz, 1 H, ArCONH), 10.60 (unresolved peak, 1 H, ArNHCO).

Elemental analysis: $C_{20}H_{25}N_3O_4S_2 \cdot 1.33CF_3CO_2H$: Calculated (%): C=46.33, H=4.52, N=7.15, S=10.91 Found (%): C=46.2, H=4.5, N=7.3, S=11.4.

EXAMPLE 3

0.74 g of S-triphenylmethyl-N-(tert-butoxycarbonyl) cysteinal, prepared according to the process described in European Patent Application EP 0,618,221, 0.1 cm³ of concentrated acetic acid and molecular sieves (3Å) are added to a solution of 0.55 g of methyl ester of N-[(5-aminonaphthyl)-1-carbonyl]-L-methionine in 30 cm³ of methanol. The reaction mixture is stirred for 20 hours at a temperature in the region of 20° C. and then 0.32 g of sodium cyanoborohydride is added. The reaction mixture is stirred for 24 hours at a temperature in the region of 20° C. and then filtered on sintered glass covered with Celite. The sintered glass is washed with methanol. The filtrate, concentrated under reduced pressure, gives a paste which is purified by chromatography on silica [eluent: dichloromethane/ethyl acetate (90/10 by volume)]. 0.3 g of the methyl ester of N-[5-(2(R)-tert-butoxycarbonylamino-3-(triphenylmethylthio)propylamino)naphthyl-1-carbonyl]-L-methionine is thus obtained in the form of a yellow solid, the characteristics of which are the following:

proton nuclear magnetic resonance spectrum (300 MHz, d6-$(CD_3)_2SO$, δ in ppm) : 1.42 (s, 9 H, $C(CH_3)_3$), 2.08 (mt, 2 H, $CH_2$), 2.10 (s, 3 H, $SCH_3$), from 2.25 to 2.55 (mt, 2 H, $CH_2S$), 2.65 (mt, 2 H, $CH_2S$), from 3.00 to 3.25 (mt, 2 H, $NCH_2$), 3.75 (s, 3 H, $COOCH_3$), 3.82 (mt, 1 H, NCH), 4.76 (mt, 1 H, CHCOO), 6.15 (unresolved peak, 1 H, ArNH), 6.52 (broad d, J=7.5 Hz, 1 H, aromatic H ortho to the amine), 7.02 (d, J=8 Hz, 1 H, OCONH), from 7.10 to 7.60 (mt, 19 H, aromatic H), 8.02 (broad d, J=8 Hz, 1 H, aromatic H ortho to the amide), 8.92 (d, J=7.5 Hz, 1 H, CONH).

0.04 g of lithium hydroxide dihydrate is added, at a temperature in the region of 5° C., to a solution of 0.3 g of the methyl ester of N-[5-(2(R)-tert-butoxycarbonylamino-3-(triphenylmethylthio)propyl-amino)naphthyl-lcarbonyl]-L-methionine in 1 cm³ of water and 10 cm³ of tetrahyrofuran. The solution is stirred for 20 hours at a temperature in the region of 20° C. and then concentrated under reduced pressure. 0.3 g of N-[5-(2(R)-tert-butoxycarbonylamino-3-(triphenylmethylthio)propylamino)naphthyl-1-carbonyl]-L-methionine is thus obtained in the form of a foam.

1.5 cm³ of trifluoroacetic acid are added, at a temperature in the region of 5° C., to a mixture of 0.3 g of N-[5-(2(R)-tert-butoxycarbonylamino-3-(triphenylmethylthio)propylamino)naphthyl-1-carbonyl}-L-methionine in 1.5 cm³ of water and 1.5 cm³ of ethanedithiol. The reaction mixture is stirred for 2 hours at a temperature in the region of 20° C. and then 15 cm³ of trifluoroacetic acid are added dropwise. The reaction mixture is stirred for 3 hours and then concentrated under reduced pressure. The residue obtained is triturated 3 times with 25 cm³ of ethyl ether and then dried under reduced pressure. 0.14 g of N-[5-(2(R)-amino-3-mercaptopropylamino)naphthyl-1-carbonyl]-L-methionine trifluoroacetate is thus obtained in the form of a yellow paste, the characteristics of which are the following:

proton nuclear magnetic resonance spectrum (200 MHz, d6-$(CD_3)_2SO$ with addition of a few drops of d4-$CD_3COOD$, δ in ppm): from 1.95 to 2.20 (mt, 2 H, $CH_2$), 2.10 (s, 3 H, $SCH_3$), from 2.50 to 2.70 (mt, 2 H, $CH_2S$), 2.88 (mt, 2 H, $CH_2S$), from 3.30 to 3.70 (mt, 3 H, $NCH_2$ and NCH), 4.59 (mt, 1 H, CHCOO), 6.30 (unresolved peak, poorly resolved ArNH), 6.71 (broad d, J=8 Hz, 1 H, aromatic H ortho to the amine), from 7.30 to 7.60 (mt, 4 H, aromatic H), 8.26 (broad d, J=8.5 Hz, 1 H, aromatic H ortho to the amide), 8.70 (d, J=9 Hz, 1 H, poorly resolved CONH).

Elemental analysis: $C_{19}H_{25}N_3O_3S_2 \cdot 1.25CF_3CO_2H$ Calculated (%): C=46.94, H=4.81, N=7.64, S=11.66 Found (%): C=46.69, H=4.32, N=7.46, S=11.90.

EXAMPLE 4

By carrying out the process as in Example 3 for the preparation of the trifluoroacetate of N-[5-(2(R)-amino-3-mercaptopropylamino)naphthyl-1-carbonyl]-L-methionine, but from 0.33 g of methyl ester of N-[5-(2(R)-tert-butoxycarbonylamino-3-(triphenylmethylthio)propylamino) naphthyl-1-carbonyl]-L-methionine, 0.05 g of trifluoroacetate of the methyl ester of N-[5-(2(R)-amino-3-mercaptopropylamino)-naphthyl-1-carbonyl]-L-methionine is obtained, the characteristics of which are the following:

proton nuclear magnetic resonance spectrum (300 MHz, d6-$(CD_3)_2SO$, δ in ppm): 2.10 (mt, 2 H, $CH_2$), 2.12 (s, 3 H, $SCH_3$), 2.63 (mt, 2 H, $CH_2S$), 2.92 (mt, 2 H, $CH_2S$), from 3.30 to 3.70 (mt, $NCH_2CHN$), 3.76 (s, 3 H, $COOCH_3$), 4.79 (mt, 1 H, CHCOO), 6.40 (unresolved peak, 1 H, ArNH), 6.72 (d, J=8 Hz, 1 H, H6), 7.40 (t, J=8 Hz, 1 H, H7), 7.52 (d, J=8 Hz, 1 H, H8), from 7.40 to 7.60 (mt, 2 H, H2, and H3), 8.13

(unresolved peak, 3 H, $NH_3^+CF_3COO^-$), 8.30 (broad d, J=8 Hz, 1 H, H4), 8.92 (d, J=7.5 Hz, 1 H, ArCONH).

Elemental analysis: $C_{20}H_{27}N_3O_3S_2$·$1.2CF_3CO_2H$ Calculated (%): C=48.18, H=5.09, N=7.52, S=11.48 Found (%): C=48.0, H=5.1, N=7.7, S=11.9.

EXAMPLE 5

By carrying out the process as in Example 1 for the preparation of the methyl ester of N-[(5-nitronaphthyl)-1-carbonyl]-L-methionine, but from 1.1 g of 5-nitronaphthalene-1-carboxylic acid and the methyl ester of L-norleucine, 1.3 g of methyl ester of N-[(5-nitronaphthyl)-1-carbonyl]-L-norleucine are obtained.

By carrying out the process as in Example 1 for the preparation of the methyl ester of N-[(5-aminonaphthyl)-1-carbonyl]-L-methionine, but from 1.3 g of methyl ester of N-[(5-nitronaphthyl)-1-carbonyl]-L-norleucine, 1.2 g of methyl ester of N-[(5-aminonaphthyl)-1-carbonyl]-L-norleucine are obtained.

By carring out the process as in Example 3 for the preparation of the methyl ester of N-[5-(2(R)-tert-butoxycarbonylamino-3-(triphenylmethylthio)propylamino)naphthyl-1-carbonyl]-L-methionine, but from 1.4 g of methyl ester of N-[(5-aminonaphthyl)-1-carbonyl]-L-norleucine, 0.67 g of methyl ester of N-[5-(2(R)-tert-butoxycarbonylamino-3-(triphenylmethylthio)propylamino)naphthyl-1-carbonyl]-L-norleucine is obtained, the characteristics of which are the following:

proton nuclear magnetic resonance spectrum (200 MHz, d6-$(CD_3)_2SO$, δ in ppm): 0.91 (t, J=7.5 Hz, 3 H, $CH_3$), from 1.25 to 1.60 (mt, 4 H, $CH_2$), 1.43 (s, 9 H, $C(CH_3)_3$), 1.80 (mt, 2 H, $CH_2$), from 2.20 to 2.70 (mt, 2 H, $CH_2S$), from 3.00 to 3.50 (mt, 2 H, $NCH_2$), 3.75 (s, 3 H, $COOCH_3$), 3.82 (mt, 1 H, NCH), 4.50 (mt, 1 H, CHCOO), 6.10 (unresolved peak, 1 H, ArNH), 6.52 (broad d, J=7.5 Hz, 1 H, aromatic H ortho to the amine), 6.97 (d, J=8.5 Hz, 1 H, OCONH), from 7.00 to 7.60 (mt, 19 H, aromatic H), 8.05 (broad d, J=8 Hz, 1 H, aromatic H ortho to the amide), 8.80 (d, J=7 Hz, 1 H, CONH).

Mass spectrum (CID): M/Z=746 ($MH^+$).

By carrying out the process as in Example 3 for the preparation of N-[5-(2 (R)-tert-butoxycarbonylamino-3-(triphenylmethylthio)propyl-amino)naphthyl-1-carbonyl]-L-methionine, but from 0.65 g of methyl ester of N-[5-(2(R)-tert-butoxycarbonylamino-3-(triphenylmethylthio)propyl-amino)naphthyl-1-carbonyl]-L-norleucine, 0.6 g of N-[5-(2(R)-tert-butoxycarbonylamino-3-(triphenylmethylthio)propylamino)naphthyl-1-carbonyl]-L-norleucine is obtained.

By carrying out the process as in Example 3 for the preparation of the trifluoroacetate of N-[5-(2(R)-amino-3-mercaptopropylamino)naphthyl-1-carbonyl]-L-methionine, but from 0.6 g of N-[5-(2(R)-tert-butoxycarbonylamino-3-(triphenylmethylthio)propyl-amino)naphthyl-1-carbonyl]-L-norleucine, 0.06 g of trifluoroacetate of N-[5-(2(R)-amino-3-mercaptopropylamino)naphthyl-1-carbonyl]-L-norleucine is obtained, the characteristics of which are the following:

proton nuclear magnetic resonance spectrum (250 MHz, d6-$(CD_3)_2SO$, δ in ppm): 0.93 (t, J=7.5 Hz, 3 H, $CH_3$), 1.40 (mt, 4 H, $CH_2$), 1.81 (mt, 2 H, $CH_2$), 2.91 (mt, 2 H, $CH_2S$), from 3.30 to 3.70 (mt, 3 H, CHN and $NCH_2$), 4.44 (mt, 1 H, CHCOO), 6.40 (unresolved peak, 1 H, ArNH), 6.71 (broad d, J=7.5 Hz, 1 H, aromatic H ortho to the amine), from 7.30 to 7.60 (mt, 4 H, aromatic H), 8.10 (unresolved peak, 2 H, $NH_2$), 8.30 (broad d, J=8 Hz, 1 H, aromatic H ortho to the amide), 8.73 (d, J=7.5 Hz, 1 H, CONH).

Elemental analysis: $C_{20}H_{27}N_3O_3S$·$CF_3CO_2H$ Calculated (%): C=52.48, H=5.60, N=8.34, S=6.37 Found (%): C=51.19, H=5.46, N=7.93, S=6.18.

Mass spectrum (LSIMS): M/Z=390 ($MH^+$)

EXAMPLE 6

By carrying out the process as in Example 1 for the preparation of the methyl ester of N-[(5-nitronaphthyl)-1-carbonyl]-L-methionine, but from 4.7 g of ethyl ester of L-methionine, 7.35 g of ethyl ester of N-[(5-nitronaphthyl)-1-carbonyl]-L-methionine are obtained, the characteristics of which are the following:

proton nuclear magnetic resonance spectrum (300 MHz, d6-$(CD_3)_2SO$, δ in ppm): 1.28 (t, J=7.5 Hz, 3 H, $CH_3$ of the ethyl), 2.08 (mt, 2 H, $CH_2$), 2.11 (s, 3 H, $SCH_3$), 2.65 (mt, 2 H, $CH_2S$), 4.22 (mt, 2 H, $COOCH_2$ of the ethyl), 4.66 (mt, 1 H, CHCOO), from 7.80 to 8.00 (mt, 3 H, H2—H3 and H7), 8.36 (d, J=7.5 Hz, 1 H, H4), 8.46 and 8.56 (2 d, J=8 Hz, 1 H, H6 and H8), 9.17 (d, J=7.5 Hz, 1 H, ArCONH).

By carrying out the process as in Example 1 for the preparation of the methyl ester of N-[(5-aminonaphthyl)-1-carbonyl]-L-methionine, but from 1.38 g of ethyl ester of N-[(5-nitronaphthyl)-1-carbonyl]-L-methionine, 1.02 g of ethyl ester of N-[(5-aminonaphthyl)-1-carbonyl]-L-methionine are obtained, which are used in the following stage without other purification.

By carring out the process as in Example 3 for the preparation of the methyl ester of N-[5-(2(R)-tert-butoxycarbonylamino-3-(triphenylmethylthio)propyl-amino)naphthyl-1-carbonyl]-L-methionine, but from 1 g of ethyl ester of N-[(5-aminonaphthyl)-1-carbonyl]-L-methionine, 0.94 g of ethyl ester of N-[5-(2(R)-tert-butoxycarbonylamino-3-(triphenylmethylthio)propyl-amino)naphthyl-1-carbonyl]-L-methionine is obtained, which are used in the following stage without other purification.

By carrying out the process as in Example 3 for the preparation of the trifluoroacetate of N-[5-(2(R)-amino-3-mercaptopropylamino)naphthyl-1-carbonyl]-L-methionine, but from 0.4 g of ethyl ester of N-[5-(2(R)-tert-butoxycarbonylamino-3-(triphenylmethylthio)-propylamino)naphthyl-1-carbonyl]-L-methionine, 0.033 g of the ethyl ester of N-[5-(2(R)-amino-3-mercaptopropylamino)naphthyl-1-carbonyl]-L-methionine is obtained in the form of a powder, the characteristics of which are the following:

proton nuclear magnetic resonance spectrum (400 MHz, d6-$(CD_3)_2SO$, δ in ppm): 1.30 (t, J=7.5 Hz, 3 H, $CH_3$ of the ethyl), 2.10 (mt, 2 H, $CH_2$), 2.11 (s, 3 H, $SCH_3$), 2.65 (mt, 2 H, $CH_2S$), 2.90 (split AB, J=14 and 5 Hz, 2 H, $CH_2S$), from 3.30 to 3.70 (mt, $NCH_2CHN$), 4.21 (mt, 2 H, $COOCH_2$ of the ethyl), 4.65 (mt, 1 H, CHCOO), 6.38 (Mt, 1 H, ArNH), 6.72 (d, J=8 Hz, 1 H, H6) 7.40 (t, J=8 Hz, 1 H, H7), 7.52 (d, J=8 Hz, 1 H, H8), from 7.40 to 7.60 (mt, 2 H, H2 and H3), 8.30 (broad d, J=8 Hz, 1 H, H4), 8.90 (d, J=7.5 Hz, 1 H, ArCONH).

Elemental analysis: $C_{21}H_{29}N_3O_3S_2$·$CF_3CO_2H$ Calculated (%): C=50.26, H=5.5, N=7.65, S=11.67 Found (%): C=49.9, H=5.8, N=7.7, S=11.7.

EXAMPLE 7

2.68 g of 5-indanol and then 0.24 g of 4-dimethylaminopiperidine and 4.96 g of 1,3- dicyclohexylcarbodiimide are added to a solution of 5.36 g of N-tert-butoxycarbonyl-L-methionine in 100 cm³ of diethyl ether. The reaction mixture is stirred at a temperature in the region of 20° C. until esterification is complete and is then filtered on sintered glass and washed successively with three times 100 cm³ of water, then with 100 cm³ of a 5% (v/v) aqueous acetic acid solution, then with 100 cm³ of water and finally with twice 100 cm³ of a 10% (w/v) aqueous sodium hydrogen carbonate solution. The organic phase is dried over magnesium sulphate, filtered and concentrated to dryness under reduced pressure. 4.03 g of the 5-indanyl ester of N-tert-butoxycarbonyl-L-methionine are obtained, which are used in the following stage without other purification.

5 cm³ of trifluoroacetic acid are added to a solution of 0.96 g of the 5-indanyl ester of N-tert-butoxycarbonyl-L-methionine in 25 cm³ of dichloromethane. The reaction mixture is stirred at a temperature in the region of 20° C. for 3 hours. After removal of the solvent and crystallization from diisopropyl ether, 0.5 g of the 5-indanyl ester of L-methionine is obtained, which are used in the following stage without other purification.

By carrying out the process as in Example 1 for the preparation of the methyl ester of N-[(5-nitronaphthyl)-1-carbonyl]-L-methionine, but from 0.5 g of the 5-indanyl ester of L-methionine, 0.28 g of the 5-indanyl ester of N-[(5-nitronaphthyl)-1-carbonyl]-L-methionine is obtained, the characteristics of which are the following:

proton nuclear magnetic resonance spectrum (250 MHz, $d6$-$(CD_3)_2SO$, δ in ppm): 2.10 (mt, 2 H, $CH_2$ of the indanyl), 2.14 (s, 3 H, $SCH_3$), 2.24 (mt, 2 H, $CH_2$), 2.73 (mt, 2 H, $CH_2S$), 2.87 and 2.90 (2 t, J=7.5 Hz, 2 H each, $ArCH_2$ of the indanyl), 4.88 (mt, 1 H, CHCOO), 6.95 (dd, J=9 and 2 Hz, 1 H, H6 of the indanyl), 7.06 (d, J=2 Hz, 1 H, H4 of the indanyl), 7.30 (d, J=9 Hz, 1 H, H7 of the indanyl) 7.76 (t, J=8 Hz, 1 H, H7), from 7.85 to 8.00 (mt, 2 H, H2 and H3), 8.35 and 8.60 (2 d, J=8 Hz, 1 H each, H6 and H8), 8.43 (dd, J=7.5 and 3 Hz, 1 H, H4), 9.36 (d, J=7.5 Hz, 1 H, ArCONH).

By carrying out the process as in Example 1 for the preparation of the methyl ester of N-[(5 -aminonaphthyl)-1-carbonyl)-L-methionine, but from 4.64 g of the 5-indanyl ester of N-[(5-nitronaphthyl)-1-carbonyl]-L-methionine, 3.40 g of the 5-indanyl ester of N-((5-aminonaphthyl)-1-carbonyl]-L-methionine are obtained, the characteristics of which are the following:

proton nuclear magnetic resonance spectrum (200 MHz, $d6$-$(CD_3)_2SO$, δ in ppm): 2.07 (mt, 2 H, $CH_2$ of the indanyl), 2.14 (s, 3 H, $SCH_3$), from 2.10 to 2.30 (mt, 2 H, $CH_2$), 2.72 (mt, 2 H, $CH_2S$), 2.88 and 2.94 (2 t, J=7 Hz, 2 H each, $ArCH_2$ of the indanyl), 4.82 (mt, 1 H, CHCOO), 5.81 (broad s, 2 H, $NH_2$), 6.72 (broad d, J=7.5 Hz, 1 H, H6) 6.94 (dd, J=8 and 2 Hz, 1 H, H6 of the indanyl) 7.05 (d, J=2 Hz, 1 H, H4 of the indanyl), 7.22 (t, J=7.5 Hz, 1 H, H7), 7.30 (d, J=8 Hz, 1 H, H7 of the indanyl), from 7.35 to 7.55 (mt, 3 H, H2—H3 and H8), 8.20 (broad d, J=8 Hz, 1 H, H4) 9.08 (d, J=7.5 Hz, 1 H, ArCONH).

By carrying out the process as in Example 3 for the preparation of the methyl ester of N-[5-(2(R)-tert-butoxycarbonylamino-3-(triphenylmethylthio)-propylamino)naphthyl-1-carbonyl]-L-methionine, but from 0.22 g of the 5-indanyl ester of N-[(5-aminonaphthyl)-1-carbonyl]-L-methionine, 0.38 g of the 5-indanyl ester of N-[5-(2(R)-tert-butoxycarbonylamino-3-(triphenylmethylthio)propylamino)naphthyl-1-carbonyl]-L-methionine is obtained, the characteristics of which are the following:

proton nuclear magnetic resonance spectrum (250 MHz, $d6$-$(CD_3)_2SO$, with addition of a few drops of $d4$-$CD_3COOD$, δ in ppm): 1.38 (s, 9 H, $OC(CH_3)_3$), 2.07 (mt, 2 H, $CH_2$ of the indanyl), 2.12 (s, 3 H, $SCH_3$), 2.25 (mt, 2 H, $CH_2$), from 2.55 to 2.80 (mt, 4 H, $CH_2S$), 2.86 and 2.90 (2 t, J=7.5 Hz, 2 H each, $ArCH_2$ of the indanyl), from 3.00 to 3.30 (mt, 2 H, $NCH_2$), 3.81 (mt, 1 H, CHN), 4.82 (mt, 1 H, CHCOO), 6.52 (broad d, J=8 Hz, 1 H, H6), 6.92 (dd, J=8 and 2 Hz, 1 H, H6 of the indanyl), 7.02 (d, J=2 Hz, 1 H, H4 of the indanyl), from 7.10 to 7.60 (mt, 20 H, H7 of the indanyl—$SC(C_6H_5)_3$—H2—H3—H7 and H8), 8.03 (broad d, J=8.5 Hz, 1 H, H4).

By carrying out the process as in Example 3 for the preparation of the trifluoroacetate of N-[5-(2(R)-amino-3-mercaptopropylamino)naphthyl-1-carbonyl]-L-methionine, but from 0.38 g of the 5-indanyl ester of N-[5-(2(R)-tert-butoxycarbonylamino-3-(triphenylmethyl-thio)propylamino)naphthyl-1-carbonyl]-L-methionine, 0.064 g of the trifluoroacetate of the 5-indanyl ester of N-[5-(2(R)-amino-3-mercaptopropylamino)naphthyl-1-carbonyl]-L-methionine is obtained, the characteristics of which are the following:

proton nuclear magnetic resonance spectrum (300 MHz, $d6$-$(CD_3)_2SO$, δ in ppm): 2.06 (mt, 2 H, $CH_2$ of the indanyl), 2.12 (s, 3 H, $SCH_3$), 2.22 (mt, 2 H, $CH_2$), 2.70 (mt, 2 H, $CH_2S$), from 2.75 to 2.85 (mt, 6 H each, $ArCH_2$ of the indanyl and $CH_2S$), from 3.00 to 3.60 (mt, $NCH_2CHN$), 4.82 (mt, 1 H, CHCOO), 6.36 (mt, 1 H, ArNH), 6.68 (broad d, J=8 Hz, 1 H, H6), 6.92 (dd, J=8 and 2 Hz, 1 H, H6 of the indanyl), 7.02 (d, J=2 Hz, 1 H, H4 of the indanyl), 7.26 (d, J=8 Hz, 1 H, H7 of the indanyl), 7.32 (t, J=8 Hz, 1 H, H7), from 7.45 to 7.65 (mt, 3 H, H2—H3 and H8), 8.26 (broad d, J=8.5 Hz, 1 H, H4), 9.10 (d, J=7.5 Hz, 1 H, ArCONH).

Elemental analysis: $C_{28}H_{33}N_3O_3S_2 \cdot CF_3CO_2H$: Calculated (%): C=56.5, H=5.37, N=6.59, S=10.06 Found (%): C=56.2, H=5.6, N=6.6, S=10.1.

EXAMPLE 8

0.048 g of benzyl alcohol and then 0.054 g of 4-dimethylaminopiperidine and 0.1 g of 1,3-dicyclo-hexylcarbodiimide are added to a solution of 0.3 g of N-[5-(2(R)-tert-butoxycarbonylamino-3-(triphenylmethyl-thio)propylamino)naphthyl-1-carbonyl]-L-methionine in 5 cm³ of diethyl ether. The reaction mixture is stirred at a temperature in the region of 20° C. until esterification is complete and then filtered on a sintered glass and washed successively three times with 100 cm³ of water, then with 100 cm³ of a 5% (v/v) aqueous acetic acid solution, then with 100 cm³ of water and finally twice with 100 cm³ of a 10% (w/v) aqueous sodium hydrogen carbonate solution. The organic phase is dried over magnesium sulphate, filtered and concentrated to dryness under reduced pressure. 0.21 g of the benzyl ester of N-[5-(2 (R)-tert-butoxycarbonyl-amino-3-(triphenylmethylthio)propylamino)naphthyl-1-carbonyl]-L-methionine is obtained, which are used in the following stage without other purification.

By carrying out the process as in Example 3 for the preparation of the trifluoroacetate of N-[5-(2(R)-amino-3-mercaptopropylamino)naphthyl-1-carbonyl]-L-methionine, but from 0.21 g of the benzyl ester of N-[5-(2(R)-tert-butoxycarbonylamino-3-(triphenylmethyl-thio)propylamino)naphthyl-1-carbonyl]-L-methionine, 0.021 g of the trifluoroacetate of the benzyl ester of N-[5-(2(R)-amino-3-mercaptopropylamino)naphthyl-1-carbonyl]-L- methionine is obtained in the form of a powder, the characteristics of which are the following:

proton nuclear magnetic resonance spectrum (200 MHz, d6-$(CD_3)_2SO$, with addition of a few drops of d4-$CD_3COOD$, δ in ppm): 2.10 (mt, 2 H, $CH_2$), 2.10 (s, 3 H, $SCH_3$), from 2.50 to 3.00 (mt, 4 H, $CH_2S$), from 3.10 to 3.90 (mt, 3 H, $NCH_2CHN$), 4.73 (mt, 1 H, CHCOO), 5.23 (limiting AB, J=13.5 Hz, 2 H, $COOCH_2Ar$), 6.32 (poorly resolved mt, ArNH), 6.70 (d, J=7.5 Hz, 1 H, H6) from 7.20 to 7.60 (mt, 9 H, aromatic H—H2—H3—H7 and H8), 8.27 (broad d, J=7.5 Hz, 1 H, H4) 8.98 (poorly resolved d, J=7.5 Hz, ArCONH).

Elemental analysis: $C_{26}H_{31}N_3O_3S_2 \cdot 1.25CF_3CO_2H$: Calculated (%): C=53.47, H=5.08, N=6.56, S=10.02 Found (%): C=53.3, H=4.9, N=6.7, S=10.2.

EXAMPLE 9

By carrying out the process as in Example 8 for the preparation of the benzyl ester of N-[5-(2(R)-tert-butoxycarbonylamino-3-(triphenylmethylthio)propyl-amino)naphthyl-1-carbonyl]-L-methionine, but from 0.053 g of 2-(2-methoxyethoxy)ethanol, 0.43 g of product is obtained which, after purification by chromatography on silica [eluent: cyclohexane/ethyl acetate (70/30 by volume), leads to 0.31 g of 2-(2-methoxyethoxy)ethyl ester of N-[5-(2(R)-tert-butoxycarbonylamino-3-(triphenylmethylthio) propylamino)naphthyl-1-carbonyl]-L-methionine, the characteristics of which are the following:

proton nuclear magnetic resonance spectrum (200 MHz, ($CDCl_3$, δ in ppm): 1.45 (s, 9 H, $OC(CH_3)_3$), 2.12 (mt, 2 H, $CH_2$), 2.12 (s, 3 H, $SCH_3$), 2.54 and 2.64 (2 mts, 2 H each, $CH_2S$), from 3.05 to 3.30 (mt, 2 H, $NCH_2$), 3.36 (s, 3 H, $COOCH_3$), from 3.40 to 4.05 (mt, 7 H, $OCH_2$ and CHN), 4.37 (mt, 2 H, $COOCH_2$), 4.68 (d, J=8 Hz, 1 H, NHCOO), 5.05 (mt, 1 H, CHCOO), 6.52 (broad d, J=7.5 Hz, 1 H, H6), 6.68 (d, J=8 Hz, 1 H, ArCONH), from 7.10 to 7.90 (mt, 21 H, $SC(C_6H_5)_3$—H2—H3—H4—H7—H8 and ArNH).

By carrying out the process as in Example 3 for the preparation of the trifluoroacetate of N-[5-(2(R)-amino-3-mercaptopropylamino)naphthyl-1-carbonyl]-L-methionine, but from 0.21 g of the 2-(2-methoxyethoxy)ethyl ester of N-[5-(2 (R)-tert-butoxycarbonylamino-3-(triphenylmethylthio)propyl-amino)naphthyl-1-carbonyl]-L-methionine, 0.051 g of trifluoroacetate of the 2-(2-methoxyethoxy)ethyl ester of N-[5-(2(R)-amino-3-mercaptopropylamino)naphthyl-1-carbonyl]-L-methionine is obtained, the characteristics of which are the following:

proton nuclear magnetic resonance spectrum (200 MHz, d6-$(CD_3)_2SO$, δ in ppm): 2.10 (mt, 2 H, $CH_2$), 2.12 (s, 3 H, $SCH_3$), 2.64 (t, J=7.5 Hz, 2 H, $CH_2S$), 2.90 (limiting AB, 2 H, $CH_2S$), 3.25 (s, 3 H, $OCH_3$), from 3.30 to 3.80 (mt, 9 H, $OCH_2$ and $NCH_2CHN$), 4.28 (mt, 2 H, $COOCH_2$), 4.67 (mt, 1 H, CHCOO), 6.32 (unresolved peak, 1 H, ArNH), 6.72 (broad d, J=8 Hz, 1 H, H6), 7.37 (t, J=8 Hz, 1 H, H7), from 7.40 to 7.65 (mt, 3 H, H2—H3 and H8), 8.09 (unresolved peak, 3 H, $NH_3^+CF_3COO^-$), 8.28 (broad d, J=8 Hz, 1 H, H4), 8.87 (d, J=7.5 Hz, 1 H, ArCONH).

Elemental analysis: $C_{24}H_{35}N_3O_5S_2 \cdot 1.25CF_3CO_2H$: Calculated (%): C=48.8, H=5.60, N=6.44, S=9.83 Found (%): C=48.8, H=5.7, N=6.6, S=10.0.

EXAMPLE 10

By carrying out the process as in Example 7 for the preparation of the 5-indanyl ester of N-tert-butoxycarbonyl-L-methionine, but from 3.73 g of 2-(phenylsulphonyl) ethanol, 7.9 g of 2-(phenylsulphonyl)ethyl ester of N-tert-butoxycarbonyl-L-methionine are obtained, which are used in the following stage without other purification.

By carrying out the process as in Example 7 for the preparation of the 5-indanyl ester of L-methionine, but from 4.17 g of 2-(phenylsulphonyl)ethyl ester of N-tert-butoxycarbonyl-L-methionine, 3.54 g of 2-(phenylsulphonyl)ethyl ester of L-methionine are obtained, which are used in the following stage without other purification.

By carrying out the process as in Example 1 for the preparation of the methyl ester of N-[(5-nitronaphthyl)-1-carbonyl]-L-methionine, but from 2.75 g of 2-(phenylsulphonyl)ethyl ester of L-methionine, 2.06 g of 2-(phenylsulphonyl)ethyl ester of N-[(5-nitronaphthyl)-1-carbonyl]-L-methionine are obtained, the characteristics of which are the following:

proton nuclear magnetic resonance spectrum (300 MHz, d6-$(CD_3)_2SO$, δ in ppm): 1.92 (mt, 2 H, $CH_2$), 2.06 (s, 3 H, $SCH_3$), 2.55 (mt, 2 H, $CH_2S$), 3.81 (t, J=6 Hz, 2 H, $CH_2SO_2$), from 4.35 to 4.55 (mt, 2 H, $COOCH_2$), 4.48 (mt, 1 H, CHCOO), 7.68 (t, J=7.5 Hz, 2 H, aromatic H meta to the sulphonyl) from 7.75 to 7.95 (mt, 4 H, H2—H3—H7 and aromatic H para to the sulphonyl), 7.96 (d, J=7.5 Hz, 2 H, aromatic H ortho to the sulphonyl) 8.34 (dd, J=7.5 and 1.5 Hz, 1 H, H4), 8.40 and 8.53 (2 broad d, J=8 Hz, 1 H each, H6 and H8), 9.09 (d, J=7.5 Hz, 1 H, ArCONH).

By carrying out the process as in Example 1 for the preparation of methyl ester of N-[(5-aminonaphthyl)-1-carbonyl)-L-methionine, but from 2.06 g of the 2-(phenylsulphonyl)ethyl ester of N-[(5-nitronaphthyl)-1-carbonyl]-L-methionine, 3.40 g of the 2-(phenylsulphonyl) ethyl ester of N-[(5-amino-naphthyl)-1-carbonyl]-L-methionine are obtained, which are used in the following stage without other purification.

By carrying out the process as in Example 3 for the preparation of the methyl ester of N-[5-(2(R)-tert-butoxycarbonylamino-3-(triphenylmethylthio)-propylamino)naphthyl-1-carbonyl]-L-methionine, but from 0.972 g of the 2-(phenylsulphonyl)ethyl ester of N-[(5-aminonaphthyl)-1-carbonyl]-L-methionine, 0.21 g of the 2-(phenylsulphonyl)ethyl ester of N-[5-(2(R)-tert-butoxycarbonylamino-3-(triphenylmethylthio)propyl-amino)naphthyl-1-carbonyl]-L-methionine is obtained, which are used in the following stage without other purification.

By carrying out the process as in Example 3 for the preparation of the trifluoroacetate of N-[5-(2(R)-amino-3-mercaptopropylamino)naphthy]-1-carbonyl]-L-methionine, but from 0.21 g of the 2-(phenylsulphonyl)ethyl ester of N-[5-(2(R)-tert-butoxycarbonylamino-3-(triphenylmethylthio)propyl-amino)naphthyl-1-carbonyl]-L-methionine, 0.013 g of the trifluoroacetate of the 2-(phenylsulphonyl)ethyl ester of N-[5-(2(R)-amino-3-mercaptopropylamino)naphthy]-1-carbonyl]-L-methionine is obtained, the characteristics of which are the following:

proton nuclear magnetic resonance spectrum (400 MHz, d6-$(CD_3)_2SO$ with addition of a few drops of d4-$CD_3COOD$, δ in ppm): 1.90 (mt, 2 H, $CH_2$), 2.05 (s, 3 H, $SCH_3$), 2.54 (mt, $CH_2S$), 2.88 (mt, 2 H, $CH_2S$), from 3.40 to 3.65 (mt, 3 H, $NCH_2CHN$), 3.76 (limiting AB, 2 H, $CH_2SO_2$), 4.38 and 4.45 (limiting AB, 1 H each, $COOCH_2$), 4.46 (mt, 1 H, CHCOO), 6.70 (d, J=7.5 Hz, 1 H, H6), 7.36 (t, J=7.5 Hz, 1 H, H7), from 7.45 to 7.60 (mt, 3 H, H2—H3 and H8), 7.68 (t, J=7.5 Hz, 2 H, aromatic H meta to the sulphonyl), 7.78 (t, J=7.5 Hz, 1 H, aromatic H para to the sulphonyl) 7.96 (d, J=7.5 Hz, 2 H, aromatic H ortho to the sulphonyl), 8.26 (broad d, J=8 Hz, 1 H, H4), 8.76 (poorly resolved d, J=7.5 Hz, ArCONH).

Mass spectrum (CID): M/Z=576 (MH$^+$)

EXAMPLE 11

1 cm$^3$ of 97% sulphuric acid is added to a suspension of 4.7 g of 5-nitro-1-naphthoic acid in 50 cm$^3$ of methanol and the reaction mixture is then brought to reflux for 12 hours. The solution is cooled to a temperature in the region of 20° C. and the precipitate formed is filtered off by centrifuge and washed twice with 5 cm$^3$ of ice-cold methanol and then dried to constant weight. 4.56 g of methyl 5-nitro-1-naphthoate are obtained, melting at 105° C. 21.5 g of tin(II) chloride dihydrate are added to a solution of 4.45 g of methyl 5-nitro-1-naphthoate in a mixture of 150 cm$^3$ of ethyl acetate and 35 cm$^3$ of ethanol. The solution is heated to a temperature in the region of 70° C. for 30 minutes and then cooled to a temperature in the region of 20° C. The reaction mixture is poured onto 200 cm$^3$ of ice and the pH of the solution is progressively brought to 7–8 by addition of a 5% (w/v) sodium hydrogen carbonate solution. The mixture obtained is filtered on a sintered glass covered with Celite, the organic phase is separated by settling and the aqueous phase is extracted twice with 150 cm$^3$ of ethyl acetate. The organic phases are combined, dried over magnesium sulphate, filtered and concentrated to dryness under reduced pressure. 4.5 g of methyl 5-amino-1-naphthoate are obtained in the form of an oil which are used in the following stage without other purification. 14.75 g of S-triphenylmethyl-N-(tert-butoxycarbonyl)cysteinal, 0.14 cm$^3$ of concentrated acetic acid, molecular sieves (3Å) and then 4.15 g of sodium cyanoborohydride are added to a solution of 4.5 g of methyl 5-amino-1-naphthoate in 30 cm$^3$ of methanol. The reaction mixture is stirred for 2 days at a temperature in the region of 20° C. and then filtered on sintered glass covered with Celite. The sintered glass is washed with methanol. The filtrate is concentrated under reduced pressure, redissolved in 150 cm$^3$ of ethyl acetate and washed with 100 cm$^3$ of a 10% (w/v) aqueous sodium hydrogen carbonate solution, with 100 cm$^3$ of a 10% (w/v) aqueous citric acid solution, with 100 cm$^3$ of distilled water, with 100 cm$^3$ of a 10% (w/v) aqueous sodium hydrogen carbonate solution and finally with 100 cm$^3$ of a saturated aqueous sodium chloride solution. The organic phase is dried over magnesium sulphate, filtered and concentrated to dryness under reduced pressure. The product is purified by chromatography on silica [eluent: cyclohexane/ethyl acetate (85/15 by volume)]. 3.5 g of methyl 5-(2(R)-tert-butoxycarbonylamino-3-(triphenylmethylthio)-propylamino)-1-naphthoate are obtained in the form of a beige foam which are used in the following stage without other purification.

3.6 cm$^3$ of methyl iodide and 7 g of solid sodium hydrogen carbonate are added, with stirring, to a solution of 1.5 g of methyl 5-(2(R)-tert-butoxycarbonylamino-3-(triphenylmethylthio)-propylamino)-1-naphthoate in 25 cm$^3$ of dimethyl-formamide. The reaction mixture is stirred for 20 hours at a temperature in the region of 20° C. and then poured onto 200 cm$^3$ of ice. The aqueous phase is extracted 3 times with 150 cm$^3$ of ethyl acetate. The organic phases are combined, dried over magnesium sulphate, filtered and concentrated to dryness under reduced pressure. The red oil obtained is purified by chromatography on silica [eluent: cyclohexane/ethyl acetate (90/10 by volume)]. 0.56 g of methyl 5-(2 (R)-tert-butoxycarbonylamino-3-(triphenylmethylthio)propyl-N-methylamino)-1-naphthoate is obtained, the characteristics of which are the following:

proton nuclear magnetic resonance spectrum (400 MHz, d6-(CD$_3$)$_2$SO, δ in ppm): 1.42 (s, 9 H, OC(CH$_3$)$_3$), 2.28 (mt, 2 H, SCH$_2$), 2.62 (s, 3 H, NCH$_3$), 2.85 and 3.04 (2 dd, J=13 and 7 Hz and J=13 and 6.5 Hz respectively, 1H each, NCH$_2$), 3.82 (mt, 1 H, CHN), 3.96 (s, 3 H, COOCH$_3$), 6.83 (d, J=9 Hz, 1 H, NHCOO), 7.15 (d, J=8 Hz, 1 H, H6), from 7.20 to 7.40 (mt, 15 H, SC(C$_6$H$_5$)$_3$), 7.47 and 7.52 (2 t, J=8 Hz, 1 H, H3 and H7), from 8.10 to 8.15 and 8.36 (mt and d respectively, J=8 Hz, 2 H and 1 H, H2—H4 and H8).

0.2 g of potassium hydroxide is added to a solution of 0.56 g of methyl 5-(2(R)-tert-butoxy-carbonylamino-3-(triphenylmethylthio)propyl-N-methyl-amino)-1-naphthoate in 25 cm$^3$ of distilled water and 55 cm$^3$ of ethanol. The solution is heated at reflux for 2 hours and then concentrated under reduced pressure. The residue is redissolved in distilled water and then brought to pH 3 with a 10% (w/v) aqueous citric acid solution. The aqueous phase is extracted 3 times with 50 cm$^3$ of ethyl acetate. The organic phases are combined, washed with a saturated aqueous sodium chloride solution, dried over magnesium sulphate, filtered and concentrated to dryness under reduced pressure. 0.55 g of 5-(2(R)-tert-butoxycarbonylamino-3-(triphenylmethylthio)propyl-N-methylamino)-1-naphthoic acid is obtained in the form of a yellow oil which are used in the following stage without other purification.

By carrying out the process as in Example 1 for the preparation of the methyl ester of N-[(5-nitronaphthyl)-1-carbonyl]-L-methionine, but from 0.55 g of 5-(2(R)-tert-butoxycarbonylamino-3-(triphenylmethylthio)propyl-N-methylamino)-1-naphthoic acid, 1.2 g of an orange oil are obtained which, after purification by chromatography on silica [eluent: cyclohexane/ethyl acetate (80/20 by volume)], lead to 0.55 g of the methyl ester of N-[5-(2(R)-tert-butoxycarbonylamino-3-(triphenylmethylthio)propyl-N-methylamino)naphthyl-1-carbonyl]-L-methionine, the characteristics of which are the following:

proton nuclear magnetic resonance spectrum (300 MHz, (CD$_3$)$_2$SO, δ in ppm): 1.41 (s, 9 H, OC(CH$_3$)$_3$), 2.06 (mt, 2 H, CH$_2$), 2.10 (s, 3 H, SCH$_3$), 2.38 (mt, 2 H, SCH$_2$), 2.60 (mt, 2 H, CH$_2$S), 2.60 (s, 3 H, NCH$_3$), 2.85 and 3.04 (2 mts, 1 H each, NCH$_2$), 3.75 (s, 3 H, COOCH$_3$), 3.82 (mt, 1 H, CHN), 4.69 (mt, 1 H, CHCOO), 6.85 (d, J=9 Hz, 1 H, NHCOO), 7.10 (d, J=8 Hz, 1 H, H6), from 7.20 to 7.45 and 7.42 (2 mts, 16 H and 1 H respectively, SC(C$_6$H$_5$)$_3$—H3 and H7), 7.55 (d, J=8 Hz, 1 H, H2), 7.85 and 7.92 (2 d, J=8 Hz, 1 H each, H4 and H8), 8.91 (d, J=7.5 Hz, 1 H, ArCONH).

By carrying out the process as in Example 3 for the preparation of N-[5-(2(R)-tert-butoxycarbonyl- amino-3-triphenylmethylthio)propylamino)naphthyl-1 -carbonyl]-L-methionine, but from 0.3 g of the methyl ester of N-[5-(2 (R)-tert-butoxycarbonylamino-3-(triphenylmethylthio) propyl-N-methylamino)naphthyl-1-carbonyl]-L-methionine. 0.3 g of N-[5-(2(R)-tert-butoxycarbonylamino-3-(triphenylmethylthio)propyl-N-methylamino)naphthyl-1-carbonyl]-L-methionine is obtained, which are used in the following stage without other purification.

By carrying out the process as in Example 3 for the preparation of the trifluoroacetate of N-[5-(2(R)-amino-3-mercaptopropylamino)naphthyl-1-carbonyl]-L-methionine, but from 0.25 g of N-[5-(2(R)-tert-butoxycarbonylamino-3-(triphenylmethylthio)propyl-N-methylamino)naphthyl-1-carbonyl]-L-methionine, 0.045 g of the trifluoroacetate of N-[5-(2(R)-amino-3-mercaptopropyl-N-methylamino) naphthyl-1-carbonyl]-L-methionine is obtained in the form of a powder, the characteristics of which are the following:

proton nuclear magnetic resonance spectrum (400 MHz, d6-(CD$_3$)$_2$SO, δ in ppm): from 1.95 to 2.15 (mt, 2 H, CH$_2$), 2.10 (s, 3 H, SCH$_3$), 2.63 (mt, 2 H, SCH$_2$), 2.78 (s, 3 H, NCH$_3$), 2.84 (mt, 2 H, CH$_2$S), 3.28 and 3.40 (2 dd, J=11 and 8 Hz and J=11 and 6 Hz respectively, 1 H each, NCH$_2$), 3.57 (mt, 1 H, CHN), 4.60 (mt, 1 H, CHCOO), 7.35 (d, J=7.5 Hz, 1 H, H6), 7.53 (t, J=8 Hz, 1 H, H7) from 7.55 to 7.70 (mt, 2 H, H2 and H3), 7.95 (unresolved peak, 2 H, NH$_2$), 7.99 (d, J=8 Hz, 1 H, H8), 8.55 (dd, J =8 and 2 Hz, 1 H, H4), 8.83 (d, J=7.5 Hz, 1 H, ArCONH).

Elemental analysis: C$_{20}$H$_{27}$N$_3$O$_3$S$_2$·1.25CF$_3$CO$_2$H: Calculated (%): C=47.9, H=5.05, N=7.45, S=11.37 Found (%): C=47.7, H=5.3, N=7.4, S=11.4.

EXAMPLE 12

By carrying out the process as in Example 3 for the preparation of the trifluoroacetate of N-[5-(2(R)-amino-3-mercaptopropylamino)naphthyl-1-carbonyl]-L-methionine, but from 0.25 g of the methyl ester of N-[5-(2(R)-tert-butoxycarbonylamino-3-(triphenylmethyl-thio)propyl-N-methylamino)naphthyl-1-carbonyl]-L-methionine, 0.049 g of the trifluoroacetate of the methyl ester of N-[5-(2(R)-amino-3-mercaptopropyl-N-methylamino)naphthyl-1-carbonyl]-L-methionine is obtained in the form of a powder, the characteristics of which are the following:

proton nuclear magnetic resonance spectrum (250 MHz, d6-(CD$_3$)$_2$SO with addition of a few drops of d4-CD$_3$COOD, δ in ppm): 2.06 (mt, 2 H, CH$_2$), 2.10 (s, 3 H, SCH$_3$), 2.63 (mt, 2 H, SCH$_2$), 2.80 (s, 3 H, NCH$_3$), 2.84 (mt, 2 H, CH$_2$S)$_1$ 3.30 and 3.42 (2 dd, J=13.5 and 9 Hz and J=13.5 and 5.5 Hz, 1 H each, NCH$_2$), 3.59 (mt, 1 H, CHN), 3.75 (s, 3 H, COOCH$_3$), 4.70 (mt, 1 H, CHCOO), 7.35 (d, J=7.5 Hz, 1 H, H6), from 7.50 to 7.70 (mt, 3 H, H2—H3 and H7), 7.97 (d, J=8.5 Hz, 1 H, H8), 8.53 (dd, J=7.5 and 2 Hz, 1 H, H4), 8.93 (d, J=7.5 Hz, 1 H, ArCONH).

Elemental analysis: C$_{21}$H$_{29}$N$_3$O$_3$S$_2$·1.25CF$_3$CO$_2$H: Calculated (%): C=48.82, H=5.27, N=7.27, S=11.09 Found (%): C=48.3, H=5.1, N=7.0 S=11.2.

EXAMPLE 13

1.5 cm$^3$ of 33% (w/w) sodium hydroxide solution, followed by 1.5 cm$^3$ of dimethyl sulphate, are added, with stirring, to a suspension of 3.75 g of S-triphenylmethyl-L-cysteine in 15 cm$^3$ of water. The reaction mixture is heated with stirring at 90° C. until a clear solution is obtained and is then heated at reflux for 2 hours. After cooling, the precipitate obtained is filtered off and washed with water and then with diethyl ether. 1.95 g of N-methyl-S-triphenylmethyl-L-cysteine are thus obtained, melting at 114° C.

0.68 cm$^3$ of triethylamine and 1.06 g of di-tert-butyl dicarbonate are added to a solution of 1.95 g of N-methyl-S-triphenylmethyl-L-cysteine in 20 cm$^3$ of dichloromethane. The reaction mixture is stirred for 20 hours at a temperature in the region of 20° C. and then washed with a 10% (w/v) aqueous citric acid solution and finally with distilled water. The organic phase is dried over magnesium sulphate, filtered and concentrated under reduced pressure. The beige solid obtained is purified by chromatography on silica [eluent: ethyl acetate]. 0.4 g of N-methyl-N-tert-butoxycarbonyl-S-triphenylmethyl-L-cysteine is obtained, the characteristics of which are the following:

proton nuclear magnetic resonance spectrum: (250 MHz, d6-(CD$_3$)$_2$SO with addition of a few drops of d4-CD$_3$COOD, at a temperature of 393 K, δ in ppm): 1.40 (s, 9 H, OC(CH$_3$)$_3$), from 2.55 to 2.82 (mt, 2 H, SCH$_2$), 2.68 (s, 3 H, NCH$_3$), 4.16 (dd, J=10 and 5.5 Hz, 1 H, CHN), from 7.20 to 7.45 (mt, 15 H, aromatic H).

1.96 cm$^3$ of N-methylpiperidine are added, at a temperature in the region of 0° C., to a suspension of 1.57 g of N,O-dimethylhydroxylamine in 10 cm$^3$ of dichloromethane. This solution is added to the reaction mixture containing 7.8 g of N-methyl-N-tert-butoxycarbonyl-S-triphenylmethyl-L-cysteine, 1.96 cm$^3$ of N-methylpiperidine and 2.08 cm$^3$ of isobutyl chloroformate in 20 cm$^3$ of dichloromethane at a temperature in the region of –8° C. The reaction mixture is stirred for 2 hours at a temperature in the region of 20° C. and then washed with a 10% (w/v) aqueous citric acid solution, then with a 2% (w/v) aqueous sodium hydroxide solution and finally with a saturated sodium chloride solution. The organic phase is dried over magnesium sulphate, filtered and concentrated under reduced pressure. The thick red oil obtained is purified by chromatography on silica [eluent: dichloromethane/ethyl acetate (95/5 by volume)]. 4.2 g of N-(N-methyl-2(R)-tert-butoxycarbonylamino-3-(triphenylmethylthio)propionyl)-N,O-dimethylhydroxylamine are obtained in the form of a red oil, the characteristics of which are the following:

proton nuclear magnetic resonance spectrum: (200 MHz, d6-(CD$_3$)$_2$SO with addition of a few drops of d4-CD$_3$COOD, at a temperature of 373 K, δ in ppm): 1.41 (s, 9 H, OC(CH$_3$)$_3$), from 2.35 to 2.75 (mt, 2 H, SCH$_2$), 2.62 (s, 3 H, NCH$_3$), 3.06 (s, 3 H, NCH$_3$), 3.60 (s, 3 H, NOCH$_3$), 4.89 (dd, J=9.5 and 6 Hz, 1 H, CHN), from 7.20 to 7.45 (mt, 15 H, aromatic H).

4.2 g of N-(-N-methyl-2(R)-tert-butoxycarbonylamino-3-(triphenylmethylthio)propionyl)-N,O-dimethylhydroxylamine in 15 cm$^3$ of diethyl ether are added, at a temperature in the region of –45° C., to a suspension of 0.386 g of lithium aluminium hydride in 35 cm$^3$ of diethyl ether. The temperature is allowed, with stirring, to rise to approximately 0° C. After cooling to a temperature in the region of –35° C., a solution of 1.77 g of sodium hydrogen carbonate in 6.5 cm$^3$ of water is added. The organic phase is washed 3 times with 10 cm$^3$ of a normal hydrochloric acid solution, then twice with 10 cm$^3$ of a saturated sodium hydrogen carbonate solution and finally with 10 cm$^3$ of a saturated sodium chloride solution. The organic phase is dried over magnesium sulphate, filtered and concentrated under reduced pressure. 2.2 g of N-methyl-N-tert-butoxycarbonyl-S-(triphenylmethyl)cysteinal are obtained, which are used in the following stage without other purification.

By carrying out the process as in Example 3 for the preparation of the methyl ester of N-[5-(2(R)- tert-butoxycarbonylamino-3-(triphenylmethylthio)propyl-amino)naphthyl-1-carbonyl]-L-methionine but from 2.9 g of N-methyl-N-tert-butoxycarbonyl-S-(triphenylmethyl)-cysteinal, 0.55 g of the methyl ester of N-{5-[(N-methyl-2(R)-tert-butoxycarbonylamino)-3-(triphenylmethylthio)propylaminolnaphthyl-1-carbonyl}-L-methionine is obtained, which are used in the following stage without other purification.

By carrying out the process as in Example 3 for the preparation of N-[5-(2(R)-tert-butoxycarbonyl-amino-3-(triphenylmethylthio)propylamino)naphthyl-1-carbonyl]-L-methionine, but from 0.35 g of methyl ester of N-{5-[(N-methyl-2(R)-tert-butoxycarbonylamino)-3-(triphenylmethylthio)propylamino]naphthyl-1-carbonyl}-L-methionine, 0.33 g of N-{5-[(N-methyl-2(R)-tert-butoxycarbonylamino)-3-(triphenylmethylthio)- propylamino]naphthyl-1-carbonyl}-L-methionine is obtained, which are used in the following stage without other purification.

By carrying out the process as in Example 3 for the preparation of the trifluoroacetate of N-[5-(2(R)-amino-3-mercaptopropylamino)naphthyl-1-carbonyl]-L-methionine, but from 0.33 g of N-{5-((N-methyl-2(R)-tert-butoxycarbonylamino)-3-(triphenylmethylthio)-propylaminolnaphthyl-1-carbonyl}-L-methionine, 0.05 g of trifluoroacetate of N-[5-(2(R)-methylamino-3-mercaptopropylamino)naphthyl-1-carbonyl]-L-methionine is obtained, the characteristics of which are the following:

proton nuclear magnetic resonance spectrum (300 MHz, d6-$(CD_3)_2SO$ with addition of a few drops of d4-$CD_3COOD$, δ in ppm): 2.08 (mt, 2 H, $CH_2$), 2.08 (s, 3 H, $SCH_3$), 2.64 (mt, 2 H, $CH_2S$), 2.68 (s, 3 H, $NCH_3$), 2.92 (mt, 2 H, $CH_2S$), from 3.30 to 3.65 (mt, 3 H, $NCH_2CHN$), 4.58 (mt, 1 H, CHCOO), 6.73 (d, J=8 Hz, 1 H, H6), 7.35 (t, J=8 Hz, 1 H, H7) from 7.45 to 7.65 (mt, 3 H, H2—H3 and H8), 8.24 (broad d, J=8.5 Hz, 1 H, H4), 8.71 (poorly resolved d, J=7.5 Hz, ArCONH).

Elemental analysis: $C_{20}H_{27}N_3O_3S_2 \cdot 1.25CF_3CO_2H$: Calculated (%): C=47.91, H=5.05, N=7.45, S=11.37 Found (%): C=47.8, H=4.7, N=7.5, S=11.5.

EXAMPLE 14

By carrying out the process as in Example 3 for the preparation of the trifluoroacetate of N-[5-(2(R)-amino-3-mercaptopropylamino)naphthyl-1-carbonyl]-L-methionine, but from 0.35 g of the methyl ester of N-{5-[(N-methyl-2(R)-tert-butoxycarbonylamino)-3-(triphenylmethylthio)propylaminolnaphthyl-1-carbonyl}-L-methionine, 0.049 g of the trifluoroacetate of the methyl ester of N-[5-(2(R)-methylamino-3-mercaptopropylamino)naphthyl-1-carbonyl]-L-methionine is obtained in the form of a powder, the characteristics of which are the following:

proton nuclear magnetic resonance spectrum (400 MHz, d6-$(CD_3)_2SO$ with addition of a few drops of d4-$CD_3COOD$, δ in ppm): 2.25 and 2.40 (2 mts, 1 H each, $CH_2$), 2.69 (s, 3 H, $SCH_3$), 2.94 (mt, 2 H, $CH_2S$), 2,94 (s, 3 H, $NCH_3$), from 3.30 to 3.65 (mt, 5 H, $CH_2S$ and $NCH_2CHN$), 3.75 (s, 3 H, $COOCH_3$), 4.72 (dd, J=9 and 4.5 Hz, 1 H, CHCOO), 6.73 (d, J=8 Hz, 1 H, H6), 7.39 (t, J=8 Hz, 1 H, H7) from 7.45 to 7.65 (mt, 3 H, H2—H3 and H8), 8.28 (broad d, J=8 Hz, 1 H, H4).

Elemental analysis: $C_{21}H_{29}N_3O_3S_2 \cdot 2.5CF_3CO_2H$: Calculated (%): C=43.33, H=4.41, N=5.83, S=8.9 Found (%): C=43.9, H=4.6, N=5.9, S=8.7.

EXAMPLE 15

2.6 g of 18-crown-6 ether, then, dropwise, a solution of 5 g of methyl ester of N-tert-butoxycarbonyl-L-methionine in 15 cm³ of tetrahydrofuran and finally 2.5 cm³ of methyl iodide are added, at a temperature in the region of 0° C., to a suspension of 12.5 g of potassium hydride in 80 cm³ of tetrahydrofuran. Stirring is continued at a temperature in the region of 0C for 2 hours. 6 cm³ of acetic acid are then added and the reaction mixture is then run onto 200 g of ice. The pH is brought to a value in the region of 9 by addition of a 10% (w/v) sodium hydroxide solution. The reaction mixture is washed 3 times with 20 cm³ of diethyl ether. The aqueous solution is brought to a pH in the region of 3 by addition of a 10% (v/v) hydrochloric acid solution and then extracted three times with 20 cm³ of ethyl acetate. The organic phases are combined and washed with a saturated sodium chloride solution, dried over magnesium sulphate, filtered and concentrated to dryness under reduced pressure. 6 g of methyl ester of N-methyl-N-tert-butoxycarbonyl-L-methionine are obtained, which are used in the following stage without other purification.

6.6 g of para-toluenesulphonic acid monohydrate are added to a solution of 4.6 g of methyl ester of N-methyl-N-tert-butoxycarbonyl-L-methionine in 150 cm³ of methanol and the reaction mixture is brought to reflux for 24 hours in the presence of molecular sieves (3Å). The reaction mixture is cooled to a temperature in the region of 20° C., then filtered on sintered glass and the solvent is removed under reduced pressure. The residue is dissolved in 150 cm³ of water and then washed with a hexane/diethyl ether (50/50 by volume) mixture. The pH of the aqueous phase is then brought to a value in the region of 10 by addition of a saturated sodium hydrogen carbonate solution. The aqueous solution is extracted four times with 50 cm³ of ethyl acetate and the organic phases are combined and washed with a saturated sodium chloride solution, dried over magnesium sulphate, filtered and concentrated to dryness under reduced pressure. 6 g of methyl ester of N-methyl-L-methionine are obtained, the characteristics of which are the following:

proton nuclear magnetic resonance spectrum (200 MHz, d6-$(CD_3)_2SO$, d in ppm): 1.75 (mt, 2 H, $CH_2$), 1.95 (unresolved peak, 1 H, NH), 2.04 (s, 3 H, $SCH_3$), 2.22 (s, 3 H, $NCH_3$), 2.52 (mt, 2 H, $CH_2S$), 3.21 (dd, J=7 and 5 Hz, 1 H, NCHCOO), 3.66 (s, 3 H, $COOCH_3$).

By carrying out the process as in Example 1 for the preparation of the methyl ester of N-[(5-nitronaphthyl)-1-carbonyl]-L-methionine, but from 0.68 g of methyl ester of N-methyl-L-methionine, 1.34 g of methyl ester of N-methyl-N-[(5-nitronaphthyl)-1-carbonyl)-L-methionine are obtained, which are used in the following stage without other purification.

By carrying out the process as in Example 1 for the preparation of the methyl ester of N-[(5-aminonaphthyl)-1-carbonyl]-L-methionine, but from 1.17 g of methyl ester of N-methyl-N-[(5-nitronaphthyl)-1-carbonyl]-L-methionine, 0.97 g of methyl ester of N-methyl-N-[(5-aminonaphthyl)-1-carbonyl]-L-methionine is obtained, which are used in the following stage without other purification.

By carrying out the process as in Example 3 for the preparation of the methyl ester of N-[5-(2(R)-tert-butoxycarbonylamino-3-(triphenylmethylthio)propylamino)naphthyl-1-carbonyl]-L-methionine, but from 0.95 g of methyl ester of N-methyl-N-[(5-aminonaphthyl)-1-carbonyl]-L-methionine, 0.97 g of methyl ester of N-methyl-N-[5-(2(R)-tert-butoxycarbonylamino-3-(triphenylmethylthio)propyl-amino)naphthyl-1-carbonyl]-L-methionine is obtained, which are used in the following stage without other purification.

By carrying out the process as in Example 3 for the preparation of N-[5-(2(R)-tert-butoxycarbonyl-amino-3-(triphenylmethylthio)propylamino)naphthyl-1-carbonyl]-L-methionine, but from 0.37 g of methyl ester of N-methyl-N-[5-(2(R)-tert-butoxycarbonylamino-3-(triphenylmethylthio)propylamino)naphthyl-1-carbonyl]-L-methionine, 0.36 g of N-methyl-N-[5-(2(R)-tert-butoxycarbonylamino-3-(triphenylmethylthio)propyl-amino)naphthyl-1-carbonyl]-L-methionine is obtained, which are used in the following stage without other purification.

By carrying out the process as in Example 3 for the preparation of N-[5-(2(R)-amino-3-mercaptopropylamino) naphthyl-1-carbonyl]-L-methionine, but from 0.35 g of N-methyl-N-[5-(2(R)-tert-butoxycarbonylamino-3-(triphenylmethylthio)propyl-amino)naphthyl-1-carbonyl]-

L-methionine, 0.13 g of N-methyl-N-[5-(2(R)-amino-3-mercaptopropyl-amino)naphthyl-1-carbonyl]-L-methionine is obtained, the characteristics of which are the following:

proton nuclear magnetic resonance spectrum (400 MHz, d6-$(CD_3)_2SO$ with addition of a few drops of d4-$CD_3COOD$, at a temperature of 413 K, δ in ppm): from 1.90 to 2.40 (mt, 5 H, $CH_2$ and $SCH_3$), from 2.40 to 2.90 (mt, 5 H, $CH_2S$ and $NCH_3$), 3.13 and 3.22 (2 dd, J=14 and 6.5 Hz, each, $CH_2S$), 3.56 and 3.76 (2 mts, 2 H and 1 H respectively, $NCH_2CHN$), 5.10 (broad unresolved peak, 1 H, CHCOO), 6.68 (d, J=8 Hz, 1 H, H6), from 7.10 to 7.50 (mt, 4 H, H2—H3—H7 and H8), 8.15 (broad d, J=8 Hz, 1 H, H4).

Elemental analysis: $C_{20}H_{27}N_3O_3S_2 \cdot 1.14CF_3CO_2H$: Calculated (%): C=48.5, H=5.14, N=7.61, S=11.62 Found (%): C=48.4, H=5.2, N=7.6, S=11.6.

EXAMPLE 16

By carrying out the process as in Example 3 for the preparation of the trifluoroacetate of N-[5-(2(R)-amino-3-mercaptopropylamino)naphthyl-1-carbonyl]-L-methionine, but from 0.34 g of methyl ester of N-methyl-N-[5-(2(R)-tert-butoxycarbonylamino-3-(triphenylmethylthio)propylamino)naphthyl-1-carbonyl]-L-methionine, 0.045 g of the methyl ester of N-methyl-N-[5-(2(R)-amino-3-mercaptopropylamino)naphthyl-1-carbonyl]-L-methionine is obtained in the form of a powder, the characteristics of which are the following:

proton nuclear magnetic resonance spectrum (400 MHz, d6-$(CD_3)_2SO$ with addition of a few drops of d4-$CD_3COOD$, at a temperature of 413 K, δ in ppm): from 1.90 to 2.30 (mt, 5 H, $CH_2$ and $SCH_3$), from 2.40 to 2.90 (mt, 5 H, $CH_2S$ and $NCH_{3\ 3}$), 3.13 and 3.22 (2 dd, J=14 and 6.5 Hz, 1 H each, $CH_2S$), from 3.45 to 3.80 (mt, 3 H, $NCH_2CHN$), 3.70 (s, 3 H, $COOCH_3$), 5.10 (broad unresolved peak, 1 H, CHCOO), 6.68 (d, J=8 Hz, 1 H, H6), from 7.10 to 7.50 (mt, 4 H, H2—H3—H7 and H8), 8.15 (broad d, J=8 Hz, 1 H, H4).

Elemental analysis: $C_{21}H_{29}N_3O_3S_2 \cdot 1.14CF_3CO_2H$: Calculated (%): C=49.42, H=5.37, N=7.43, S=11.33 Found (%): C=49.4, H=5.0, N=7.5, S=11.5.

EXAMPLE 17

6-Nitronaphthalene-1-carboxylic acid is prepared according to the method of T. Nakayama et al., Chem. Pharm. Bull., 32, 3968 (1984).

9.9 g of L-methionine methyl ester hydrochloride, 6.8 g of 1-hydroxybenzotriazole, 5 $cm^3$ of triethylamine and 10.3 g of dicyclohexylcarbodiimide are added to a solution of a mixture of 9.84 g of 6-nitronaphthalene-1-carboxylic acid and 3-nitronaphthalene-1-carboxylic acid in 200 $cm^3$ of chloroform and 60 $cm^3$ of dimethylformamide. The reaction mixture is stirred for 2 days at a temperature in the region of 20° C., then filtered on sintered glass and washed with 50 $cm^3$ of chloroform. The organic solution is washed twice with 200 $cm^3$ of a 10% (w/v) aqueous sodium bicarbonate solution, then with a 10% (w/v) aqueous citric acid solution, [lacuna] with distilled water and then with a saturated aqueous sodium chloride solution. The organic phase is dried over magnesium sulphate, filtered and then concentrated to dryness under reduced pressure. 13.3 g of an oil are obtained, which oil is purified by chromatography on silica, elution being carried out with a cyclohexane/ethyl acetate (1/1 by volume) mixture. 0.64 g of the methyl ester of N-[(6-nitronaphthyl)-1-carbonyl]-L-methionine, in the form of a solid, and 3.7 g of a mixture of the methyl ester of N-[(6-nitronaphthyl)-1-carbonyl]-L-methionine and the methyl ester of N-[(3-nitronaphthyl)-1-carbonyl]-L-methionine are thus obtained.

The methyl ester of N-[(6-nitronaphthyl)-1-carbonyl]-L-methionine has the characteristics are the following:

proton nuclear magnetic resonance spectrum (300 MHz, d6-$(CD_3)_2SO$, δ in ppm): from 2.10 (mt, 2 H, $CH_2$), 2.12 (s, 3 H, $SCH_3$), 2.65 (mt, 2 H, $CH_2S$), 3.77 (s, 3 H, $COOCH_3$), 4.70 (mt, 1 H, CHCOO), 7.82 (t, J=7.5 Hz, 1 H, H at 3), 7.95 and 8.45 (2 d, J=7.5 Hz, 1 H each, H at 2 and 4), 8.36 (dd, J=9 and 2 Hz, 1 H, H at 7), 8.48 (broad d, J=9 Hz, 1 H, H at 8), 9.12 (d, J=2 Hz, 1 H, H at 5), 9.18 (d, J=7.5 Hz, 1 H, CONH).

2 g of tin(II) chloride dihydrate are added to a solution of 0.64 g of the methyl ester of N-[(6-nitronaphthyl)-1-carbonyl]-L-methionine in 40 $cm^3$ of ethanol. The reaction mixture is stirred for 30 minutes at a temperature in the region of 70° C. and then cooled to a temperature in the region of 20° C. 40 $cm^3$ of ethyl acetate are added. The reaction mixture is poured onto ice and then brought to a pH in the region of 7–8 by addition of a 5% (w/v) aqueous sodium hydrogen addition of a 5% (w/v) agueous sodium hydrogen carbonate solution. The mixture obtained is filtered on sintered glass covered with Celite. The organic phase is separated by settling and the aqueous phase is extracted 3 times with 150 $cm^3$ of ethyl acetate. The organic phases are combined, dried over magnesium sulphate, filtered and concentrated to dryness under reduced pressure. 0.66 g of an oil is thus obtained, which oil is purified by chromatography on silica, elution being carried out with a cyclohexane/ethyl acetate (1/1 by volume) mixture. 0.38 g of methyl ester of N-[(6-aminonaphthyl)-1-carbonyl]-L-methionine is thus obtained in the form of an oil, the characteristics of which are the following:

proton nuclear magnetic resonance spectrum (200 MHz, d6-$(CD_3)_2SO$, δ in ppm): 2.06 (mt, 2 H, $CH_2$), 2.09 (s, 3 H, $SCH_3$), 2.60 (mt, 2 H, $CH_2S$), 3.80 (s, 3 H, $COOCH_3$), 4.63 (mt, 1 H, CHCOO), 5.48 (s, 2 H, Ar—$NH_2$), 6.86 (dd, J=9 and 2 Hz, 1 H, H at 7), from 7.19 to 7.62 (2 d, J=8 Hz, 1 H each, H at 2 and 4), 7.32 (t, J=8 Hz, 1 H, H at 3) 7.90 (broad d, J=9 Hz, 1 H, H at 8), 8.82 (d, J=7.5 Hz, 1 H, CONH).

1.02 g of S-triphenylmethyl-N-(tert-butoxycarbonyl)cysteine, 0.297 g of 1-hydroxybenzotriazole and 0.42 g of 1-(3-diethylaminopropyl)-3-ethylcarbodiimide hydrochloride are added to a solution of 0.66 g of methyl ester of N-[(6-aminonaphthyl)-1-carbonyl]-L-methionine in 20 $cm^3$ of dichloromethane. The reaction mixture is stirred for 24 hours at a temperature in the region of 20° C. The solution is washed 3 times with 15 $cm^3$ of distilled water. The organic phase is dried over magnesium sulphate, filtered and concentrated to dryness under reduced pressure. A foam is obtained which is purified by chromatography on silica [eluent: dichloromethane/ethyl acetate (8/2 by volume)]. 0.6 g of the methyl ester of N-[6-(2(R)-tert-butoxycarbonylamino-3-triphenylmethylthio)propionyl-amino)naphthyl-1-carbonyl]-L-methionine is obtained in the form of a white solid, the characteristics of which are the following:

proton nuclear magnetic resonance spectrum (400 MHz, $CDCl_{13}$, at a temperature of 333 K, δ in ppm): 1.45 (s, 9 H, $OC(CH_3)_3$), 2.14 (s, 3 H, $SCH_3$), 2.16 and 2.35 (2 mts, 1 H each, $CH_2$), 2.55 (t, J=7.5 Hz, 2 H, $CH_2S$), 2.73 and 2.83 (2 dd, J=13 and 5.5 Hz and J=13 and 7.5 Hz respectively, 1 H each, $CH_2S$), 3.83 (s, 3 H, COOCH$_3$), 3.99 (mt, 1 H, CHN), 4.84 (d, J=7.5 Hz, 1 H, NHCOO), 5.03 (mt, 1 H, CHCOO), 6.64 (d, J=8 Hz, 1 H, ArCONH), from 7.05 to 7.50 (mt, 16 H, SC(C$_6$H$_5$)$_3$ and H3), 7.38 (dd, J=9 and 1.5 Hz, 1 H, H7), 7.59 (d, J=7.5 Hz, 1 H, H2), 7.85 (broad d, J=7.5 Hz, 1 H, H4), 8.22 (unresolved peak, 1 H, ArNHCO), 8.27 (d, J=1.5 Hz, 1 H, H5), 8.33 (d, J=9 Hz, 1 H, H8).

0.057 g of lithium hydroxide hydrate is added to a solution of 0.3 g of methyl ester of N-[6-(2(R)-tert-butoxycarbonylamino-3-(triphenylmethylthio) propionylamino)naphthyl-1-carbonyl]-L-methionine in 0.75 cm$^3$ of distilled water and 7.5 cm$^3$ of tetrahydrofuran. The solution is stirred for 20 hours at a temperature in the region of 20° C. and then concentrated under reduced pressure. 0.29 g of N-[6-(2(R)-tert-butoxycarbonylamino-3-(triphenylmethylthio)propionylamino)naphthyl-1-carbonyl]-L-methionine is obtained in the form of a foam. This product is used in the following stage without other purification.

0.1 cm$^3$ of triethylsilane and then 2.6 cm$^3$ of trifluoroacetic acid are added, at a temperature in the region of 20° C., to a mixture of 0.29 g of N-[6-(2(R)-tert-butoxycarbonylamino-3-(triphenylmethylthio) propionylamino)naphthyl-1-carbonyl]-L-methionine in 2.6 cm$^3$ of dichloromethane. The reaction mixture is stirred for 2 hours at a temperature in the region of 20° C. and then concentrated under reduced pressure. The residue is triturated 3 times with 25 cm$^3$ of hexane, 3 times with 25 cm$^3$ of pentane and 3 times with 25 cm$^3$ of ethyl ether and then dried under reduced pressure. The residue is purified by high performance liquid chromatography (C18 phase), elution being carried out with an acetonitrile/water mixture containing 0.1% of trifluoroacetic acid. 0.02 g of N-t6-(2(R)-amino-3-mercaptopropionyl- amino)naphthyl-1-carbonyl]-L-methionine trifluoroacetate is obtained in the form of a powder, the characteristics of which are the following:

proton nuclear magnetic resonance spectrum (300 MHz, d6-(CD$_3$)$_2$SO, δ in ppm): 2.08 (mt, 2 H, CH$_2$) , 2.11 (S, 3 H, SCH$_3$), 2.63 (mt, 2 H, CH$_2$S), 3.11 (mt, 2 H, CH$_2$S), 4.22 (mt, 1H, CHN), 4.61 (mt, 1 H, CHCOO), 7.58 (mt, 2 H, H2 and H3), 7.68 (dd, J=9 and 2.5 Hz, 1 H, H7), 8.01 (dd, J=7.5 and 2.5 Hz, 1 H, H4), 8.28 (d, J=9 Hz, 1 H, H8), 8.38 (d, J=2.5 Hz, 1 H, H5), 8.43 (unresolved peak, 3 H, NH$_3^+$CF$_3$COO$^-$), 8.88 (d, J=7.5 Hz, 1 H, ArCONH), 10.82 (s, 1 H, ArNHCO).

Elemental analysis: C$_{19}$H$_{23}$N$_3$O$_4$S$_2$·1CF$_3$CO$_2$H: Calculated (%): C=47.1, H=4.52, N=7.85, S=11.9 Found (%): C=47.1, H=4.3, N=7.6, S=10.7.

EXAMPLE 18

By carrying out the process as in Example 17 for the preparation of the trifluoroacetate of N-[6-(2(R)-amino-3-mercaptopropionylamino)naphthyl-1-carbonyl]-L-methionine, but from 0.25 g of the methyl ester of N-[6-(2 (R)-tert-butoxycarbonylamino-3-(triphenylmethylthio) propionylamino)naphthyl-1 -carbonyl]-L-methionine, 0.035 g of trifluoroacetate of the methyl ester of N-[6-(2(R)-amino-3-mercaptopropionylamino)naphthyl-1-carbonyl]-L-methionine is obtained, the characteristics of which are the following:

proton nuclear magnetic resonance spectrum (400 MHz, d6-(CD$_3$)$_2$SO, δ in ppm): 2.08 (mt, 2 H, CH$_2$), 2.10 (s, 3 H, SCH$_3$), 2.64 (mt, 2 H, CH$_2$S), 3.11 (d, J=6 Hz, 2 H, CH$_2$S), 3.74 (s, 3 H, COOCH$_3$), 4.19 (t, J=6 Hz, 1 H, CHN), 4.67 (mt, 1 H, CHCOO), from 7.50 to 7.60 (mt, 2 H, H2 and H3), 7.68 (dd, J=9 and 1.5 Hz, 1 H, H7), 8.00 (broad d, J=8 and 2 Hz, 1 H, H4), 8.23 (d, J=9 Hz, 1 H, H8), 8.36 (d, J=1.5 Hz, 1 H, H5), 8.43 (unresolved peak, 2 H, NH$_2$), 8.98 (d, J=8 Hz, 1 H, ArCONH), 10.78 (s, 1 H, ArNHCO).

Elemental analysis: C$_{20}$H$_{25}$N$_3$O$_4$S$_2$·1CF$_3$CO$_2$H: Calculated (%): C=48.08, H=4.77, N=7.65, S=11.6 Found (%): C=48.3, H=4.6, N=7.5, S=11.2.

EXAMPLE 19

1.34 g of S-triphenylmethyl-N-(tert-butoxycarbonyl) cysteinal, prepared according to the process described in Patent EP 0,618,221 A2, 0.17 cm$^3$ of acetic acid, of molecular sieves (3Å) and then 0.19 g of sodium cyanoborohydride are added to a solution of 0.34 g of methyl ester of N-[(6-aminonaphthyl)-1-carbonyl]-L-methionine in 20 cm$^3$ of methanol. The reaction mixture is stirred for 3 days at a temperature in the region of 20° C. and then filtered on sintered glass covered with Celite. The sintered glass is washed with methanol. The filtrate is concentrated under reduced pressure, redissolved in 100 cm$^3$ of ethyl acetate and washed with 100 cm$^3$ of a 10% (w/v) aqueous sodium hydrogen carbonate solution, 80 cm$^3$ of a 10% (w/v) aqueous citric acid solution, 100 cm$^3$ of distilled water, again with 100 cm$^3$ of a 10% (w/v) aqueous sodium hydrogen carbonate solution and finally with 100 cm$^3$ of a saturated aqueous sodium chloride solution. The organic phase is dried over magnesium sulphate, filtered and concentrated to dryness under reduced pressure. A foam is obtained which is purified by chromatography on silica [eluent: cyclohexane/ethyl acetate (1/3 by volume)]. 0.48 g of the methyl ester of N-[6-(2(R)-tert-butoxycarbonylamino-3-(triphenylmethylthio)propylamino)naphthyl-1-carbonyl]-L-methionine is obtained in the form of a yellow solid, the characteristics of which are the following:

proton nuclear magnetic resonance spectrum (300 MHz, d6-(CD$_3$)$_2$SO, δ in ppm): 1.40 (s, 9 H, (CH$_3$)$_3$), 2.10 (mt, 2 H, CH$_2$), 2.12 (s, 3 H, SCH$_3$), from 2.20 to 2.55 and 2.63 (2 mts, 2 H each, CH$_2$S), 3.06 (mt, 2 H, NCH$_2$), 3.74 (mt, 1 H, CHN), 3.74 (s, 3 H, COOCH$_3$), 4.67 (mt, 1 H, CHCOO), 5.92 (broad t, J=5.5 Hz, 1 H, ArNH), 6.75 (broad s, 1 H, H5), 6.89 and 7.63 (2 d, J=7.5 Hz, 1 H each, H at 2 and H at 4), 6.95 (dd, J=9 and 1.5 Hz, 1 H, H at 7), from 7.20 to 7.45 (mt, 16 H, H at 3 and aromatic H), 7.93 (broad d, J=9 Hz, 1 H, H at 8), 8.85 (d, J=7.5 Hz, 1 H, CONH).

0.05 g of lithium hydroxide hydrate is added to a solution of 0.48 g of methyl ester of N-[6-(2(R)-tert-butoxycarbonylamino-3-(triphenylmethylthio)propyl-amino)naphthyl-1-carbonyl]-L-methionine in 2.6 cm$^3$ of distilled water and 7.2 cm$^3$ of tetrahydrofuran. The solution is stirred for 20 hours at a temperature in the region of 20° C. and then concentrated under reduced pressure. The residue is dissolved in distilled water and then brought to pH=3 by addition of a 10% (w/v) aqueous citric acid solution. The aqueous phase is extracted 3 times with 50 cm$^3$ of ethyl acetate. The organic phases are combined, washed with a saturated aqueous sodium chloride solution, dried over magnesium sulphate, filtered and concentrated to dryness under reduced pressure. 0.43 g of N-[6-(2(R)-tert-butoxycarbonylamino-3-(triphenylmethylthio)propyl-amino)naphthyl-1-carbonyl]-L-methionine is obtained in the form of a foam. This product is used in the following stage without other purification.

20 cm$^3$ of trifluoroacetic acid are added, at a temperature in the region of 20° C., to a mixture of 0.42 g of N-[6-(2 (R)-tert-butoxycarbonylamino-3-(triphenylmethylthio) propylamino)naphthyl-1-carbonyl]-L-methionine in 1.0 cm$^3$ of ethanedithiol. The reaction mixture is stirred for 2 hours at a temperature in the region of 20° C. and then concentrated under reduced pressure. The residue is triturated 3 times with 25 cm³ of ethyl ether and then dried under reduced pressure. The residue is purified by high performance liquid chromatography (C18 phase), elution being carried out with an acetonitrile/water mixture containing 0.1% of trifluoroacetic acid. 0.14 g of trifluoroacetate of N-(6-(2(R)-amino-3-mercaptopropylamino)naphthyl-1-carbonyl]-L-methionine is obtained in the form of a powder, the characteristics of which are the following:

proton nuclear magnetic resonance spectrum (300 MHz, d6-$(CD_3)_2SO$, δ in ppm): 2.05 (mt, 2 H, $CH_2$), 2.10 (s, 3 H, $SCH_3$), 2.62 and 2.88 (2 mts, 2 H each, $CH_2S$), from 3.30 to 3.70 (mt, 3 H, CHN and $NCH_2$), 4.58 (mt, 1 H, CHCOO), 6.20 (unresolved peak, 1 H, ArNH), 6.92 (broad s, 1 H, H at 5), 7.05 (dd, J=9 and 1.5 Hz, 1 H, H at 7), 7.28 and 7.70 (2 d, J=7.5 Hz, 1 H each, H at 2 and H at 4), 7.40 (t, J=7.5 Hz, 1 H, H at 3), 8.08 (broad d, J=9 Hz, 1 H, H at 8), 8.09 (unresolved peak, 3 H, $NH_3^+$), 8.70 (d, J=7.5 Hz, 1 H, CONH).

Elemental analysis: $C_{19}H_{25}N_3O_3S_2 \cdot 1.4CF_3CO_2H$: Calculated (%): C=46.16, H=4.69, N=7.41, S=11.31 Found (%): C=46.13, H=4.59, N=7.45, S=11.25.

EXAMPLE 20

By carrying out the process as in Example 19 for the preparation of the trifluoroacetate of N-[6-(2(R)-amino-3-mercaptopropylamino)naphthyl-1-carbonyl]-L-methionine, but from 0.6 g of methyl ester of N-[6-(2(R)-tert-butoxycarbonylamino-3-(triphenylmethylthio)-propylamino)naphthyl-1-carbonyl]-L-methionine, 0.15 g of trifluoroacetate of the methyl ester of N-[6-(2(R)-amino-3-mercaptopropylamino)naphthyl-1-carbonyl]-L-methionine is obtained, the characteristics of which are the following:

proton nuclear magnetic resonance spectrum (300 MHz, d6-$(CD_3)_2SO$ with addition of a few drops of d4-$CD_3COOD$, δ in ppm): 2.05 (mt, 2 H, $CH_2$), 2.05 (s, 3 H, $SCH_3$), 2.56 and 2.83 (2 mts, 2 H each, $CH_2S$), from 3.35 to 3.60 (mt, 3 H, CHN and $NCH_2$), 3.68 (s, 3 H, $COOCH_3$), 4.54 (mt, 1 H, CHCOO), 6.90 (d, J=1.5 Hz, 1 H, H at 5), 7.03 (dd, J=9 and 1.5 Hz, 1 H, H at 7), 7.28 and 7.67 (2 d, J=7.5 Hz, 1 H each, H at 2 and H at 4), 7.34 (t, J=7.5 Hz, 1 H, H at 3), 8.00 (broad d, J=9 Hz, 1 H, H at 8).

Elemental analysis: $C_{20}H_{27}N_3O_3S_2 \cdot 1.2CF_3CO_2H$: Calculated (%): C=48.19, H=5.09, N=7.52, S=11.48 Found (%): C=48.05, H=4.98, N=7.75, S=11.80.

EXAMPLE 21

0.5 g of methyl ester of N-[(6-nitronaphthyl)-1-carbonyl]-L-methionine, dissolved in 4 cm³ of dichloromethane, is added dropwise, over a period of 10 minutes, at a temperature in the region of 0C, to a solution of 0.57 g of meta-chloroperbenzoic acid in 6 cm³ of dichloromethane. The reaction mixture is stirred for 20 hours at a temperature in the region of 20° C., is then cooled to a temperature in the region of 0° C. and 5 cm³ of a normal sodium hydroxide solution are added. After separation by settling, the aqueous phase is extracted twice with 10 cm³ of dichloromethane. The organic phases are combined, washed with a saturated aqueous sodium chloride solution, dried over magnesium sulphate, filtered and concentrated to dryness under reduced pressure. 0.6 g of methyl 2(S)-(6-nitro-1-naphthoylamino)-4-(methylsulphonyl)butanoate is obtained, which are used in the following stage without other purification.

0.04 g of 10% palladium-on-charcoal is added to a solution of 0.42 g of methyl ester of methyl 2(S)-(6-nitro-1-naphthoylamino)-4-(methylsulphonyl)butanoate dissolved in 30 cm³ of ethyl acetate and 20 cm³ of ethanol and the solution is subjected to a hydrogen pressure of 1.5 atmosphere for 3 hours at a temperature in the region of 20° C. The reaction mixture is filtered on sintered glass covered with Celite and concentrated to dryness under reduced pressure. 0.6 g of methyl 2(S)-(6-amino-1-naphthoylamino)-4-(methylsulphonyl)-butanoate is obtained, the characteristics of which are the following:

nuclear magnetic resonance spectrum (300 MHz, d6-$(CD_3)_2SO$ with addition of a few drops of d4-$CD_3COOD$, δ in ppm): from 2.10 to 2.40 (mt, 2 H, $CH_2$), 3.00 (s, 3 H, $SO_2CH_3$), from 3.15 to 3.40 (mt, 2 H, $CH_2SO_2$), 3.75 (s, 3 H, $COOCH_3$), 4.67 (mt, 1 H, CHCOO), 6.89 (d, J=2 Hz, 1 H, H5), 7.01 (dd, J=9 and 2 Hz, 1 H, H7), 7.25 (broad d, J=7.5 Hz, 1 H, H2), 7.32, (t, J=7.5 Hz, 1 H, H3), 7.63 (broad d, J=7.5 Hz, 1 H, H4), 7.95 (d, J=9 Hz, 1 H, H8), 8.85 (poorly resolved d, J=7.5 Hz, ArCONH).

By carrying out the process as in Example 19 for the preparation of the methyl ester of N-[6-(2(R)-tert-butoxycarbonylamino-3-(triphenylmethylthio)propyl-amino)naphthyl-1-carbonyl]-L-methionine, but from 0.4 g of methyl 2(S)-($^6$-amino-1-naphthoylamino)-4-(methylsulphonyl)butanoate, 0.55 g of methyl 2(S)-[6-(2(R)-tert-butoxycarbonylamino-3-(triphenylmethylthio)-propylamino)-1-naphthoylamino]-4-(methylsulphonyl)-butanoate is obtained, the characteristics of which are the following:

nuclear magnetic resonance spectrum (300 MHz, d6-$(CD_3)_2SO$, δ in ppm): 1.40 (s, 9 H, $OC(CH_3)_3$, from 2.20 to 2.45 (mt, 2 H, $CH_2$), from 2.50 to 2.65 (mt, $CH_2S$), 3.03 (s, 3 H, $SO_2CH_3$), from 2.95 to 3.40 (mt, 4 H, $NCH_2$ and $CH_2SO_2$), from 3.70 to 3.85 (mt, 1 H, CHN), 3.77 (s, 3 H, $COOCH_3$) 4.68 (mt, 1 H, CHCOO), 5.92 (broad t, J=5 Hz, 1 H, ArNH), 6.75 (broad s, 1 H, H5) 6.90 (d, J=8 Hz, 1 H, NHCOO), 6.94 (broad d, J=9 Hz, 1 H, H7), from 7.25 to 7.45 (mt, 17 H, $SC(C_6H_5)_3$—H2 and H3), 7.65 (broad d, J=7.5 Hz, 1 H, H4), 7.95 (d, J=9 Hz, 1 H, H8), 8.94 (d, J=7.5 Hz, 1 H, ArCONH).

By carrying out the process as in Example 19 for the preparation of N-[6-(2(R)-tert-butoxycarbonyl-amino-3-(triphenylmethylthio)propylamino)naphthyl-1- carbonyl]-L-methionine, but from 0.36 g of methyl 2(S)-[6-(2(R)-tert-butoxycarbonylamino-3-(triphenyl-methylthio)propylamino)-1-naphthoylamino]-4-(methylsulphonyl) butanoate, 0.35 g of 2(S)-[6-(2(R)-tert-butoxycarbonylamino-3-(triphenylmethylthio)-propylamino)-1-naphthoylamino]-4-(methylsulphonyl)-butanoic acid is obtained, which are used in the following stage without other purification.

By carrying out the process as in Example 19 for the preparation of the trifluoroacetate of N-[6-(2(R)-amino-3-mercaptopropylamino)naphthyl-1-carbonyl]-L-methionine, but from 0.35 g of 2(S)-[6-(2(R)-tert-butoxycarbonylamino-3-(triphenylmethylthio)-propylamino)-1-naphthoylamino]-4-(methylsulphonyl)-butanoic acid, 0.132 g of trifluoroacetate of 2(S)-[6-(2(R)-amino-3-mercaptopropylamino)-1-naphthoylamino]-4-(methylsulphonyl)butanoic acid is obtained, the characteristics of which are the following:

nuclear magnetic resonance spectrum (300 MHz, d6-$(CD_3)_2SO$, δ in ppm): from 2.10 to 2.45 (mt, 2 H, $CH_2$), 2.90 (mt, 2 H, $CH_2S$), 3.04 (s, 3 H, $SO_2CH_3$), from 3.15 to 3.70 (mt, $CH_2SO_2$ and $NCH_2CHN$), 4.60 (mt, 1 H, CHCOO), 6.24 (unresolved peak, 1 H, ArNH), 6.94 (d, J=2 Hz, 1 H, H5), 7.08 (dd, J=9 and 2 Hz, 1 H, H7), 7.35 (broad d, J=7.5 Hz, 1 H, H2), 7.42 (t, J=7.5 Hz, 1 H, H3), 7.72 (broad d, J=7.5 Hz, 1 H, H4), 8.05 (d, J=9 Hz, 1 H, H8), 8.08 (unresolved peak, 3 H, $NH_3^+$ $CF_3COO^-$), 8.83 (d, J=7.5 Hz, 1 H, ArCONH).

Elemental analysis: $C_{19}H_{25}N_3O_5S_2 \cdot 1.6CF_3CO_2H$: Calculated (%): C=42.87, H=4.31, N=6.76, S=10.31 Found (%): C=42.4, H=4.2, N=6.9, S=10.4.

EXAMPLE 22

By carrying out the process as in Example 19 for the preparation of the trifluoroacetate of N-[6-(2(R)-amino-³-mercaptopropylamino)naphthyl-1-carbonyl]- L-methionine, but from 0.16 g of methyl 2(S)-[6-(2(R)-tert-butoxycarbonylamino-3-(triphenylmethylthio)-propylamino)-1-naphthoylamino]-4-(methylsulphonyl)-butanoate, 0.035 g of trifluoroacetate of methyl 2(S)-[6-(2(R)-amino-³-mercaptopropylamino)-1-naphthoyl-amino]-⁴-(methylsulphonyl)butanoate is obtained, the characteristics of which are the following:

nuclear magnetic resonance spectrum (300 MHz, d6-$(CD_3)_2SO$, δ in ppm): from 2.25 to 2.40 (mt, 2 H, $CH_2$), 2.91 (mt, 2 H, $CH_2S$), 3.04 (s, 3 H, $SO_2CH_3$), from 3.20 to 3.65 (mt, $CH_2SO_2$ and $NCH_2CHN$), 3.77 (s, 3 H, $COOCH_3$), 4.67 (mt, 1 H, CHCOO), 6.24 (unresolved peak, 1 H, ArNH), 6.94 (d, J=2 Hz, 1 H, H5), 7.08 (dd, J=9 and 2 Hz, 1 H, H7), 7.35 (broad d, J=7.5 Hz, 1 H, H2), 7.42 (t, J=7.5 Hz, 1 H, H3), 7.65 (broad d, J=7.5 Hz, 1 H, H4), 8.05 (d, J=9 Hz, 1 H, H8), 8.08 (unresolved peak, 3 H, $NH_3^+CF_3COO^-$), 8.95 (d, J=7.5 Hz, 1 H, ArCONH).

Elemental analysis: $C_{20}H_{27}N_3O_5S_2 \cdot 1.25CF_3CO_2H$: Calculated (%): C=45.34, H=4.78, N=7.05, S=10.76 Found (%): C=44.4, H=4.4, N=7.0, S=10.7.

EXAMPLE 23

By carrying out the process as in Example 17 for the preparation of the methyl ester of N-[6-(2(R)-tert-butoxycarbonylamino-3-(triphenylmethylthio)-propionylamino)naphthyl-1-carbonyl]-L-methionine, but from 0.66 g of methyl ester of N-[(6-aminonaphthyl)-1-carbonyl]-L-methionine and 0.48 g of N,N'-di(tert-butoxycarbonyl)cystine, 0.7 g of dimethyl ester of di{N-[6-(2(R)-tert-butoxycarbonylamino-3-sulphanylpropionylamino)naphthyl-1-carbonyl]-L-methionine} is obtained, which are used in the following stage without other purification.

By carrying out the process as in Example 17 for the preparation of the trifluoroacetate of N-[6- (2(R)-amino-3-mercaptopropionylamino)naphthyl-1- carbonyl]-L-methionine, but from 0.3 g of dimethyl ester of di{N-[6-(2(R)-tert-butoxycarbonylamino-3-sulphanylpropionylamino) naphthyl-1-carbonyl]-L-methionine}, 0.06 g of trifluoroacetate of the dimethyl ester of di{N-[6-(2(R)-amino-3 -sulphanylpropionyl-amino)naphthyl-1-carbonyl]-L-methionine} is obtained, the characteristics of which are the following:

proton nuclear magnetic resonance spectrum (400 MHz, d6-$(CD_3)_2SO$, δ in ppm): from 2.00 to 2.15 (mt, 2 H, $CH_2$), 2.08 (s, 3 H, $SCH_3$) 2.62 (mt, 2 H, $CH_2S$), 3.22 and 3.44 (dd and mt respectively, J=14 and 8 Hz, 1 H each, $CH_2S$), 3.72 (s, 3 H, $COOCH_3$), 4.32 (mt, 1 H, CHN), 4.67 (mt, 1 H, CHCOO), from 7.50 to 7.60 (mt, 2 H, H2 and H3), 7.68 (dd, J=9 and 2 Hz, 1 H, H7), 7.97 (broad d, J=8.5 Hz, 1 H, H4), 8.24 (d, J=9 Hz, 1 H, H8), 8.35 (d, J=2 Hz, 1 H, H5), 8.53 (unresolved peak, 2 H, $NH_3^+CF_3COO^-$), 8.98 (d, J=8 Hz, 1 H, ArCONH), 10.92 (s, 1 H, ArNHCO).

Elemental analysis: $C_{40}H_{48}N_6O_8S_4 \cdot 2CF_3CO_2H$ dihydrate: Calculated (%): C=46.6, H=4.75, N=7.4, S=11.3 Found (%): C=46.6, H=4.5, N=7.1, S=11.0.

The inhibitory activity with respect to farnesyl transferase and to farnesylation of the Ras protein may be demonstrated in the following test:

Farnesyl transferase activity is determined by the quantity of [³H] farnesyl transferred from [³H]farnesyl pyrophosphate ([³H]FPP) to the p21 H-Ras protein. The standard reaction mixture is composed, for a final volume of 60 μl, of 50 mM Tris-HCl, 5 mM $MgCl_2$, 5 mM dithiothreitol, 0.2% octyl β-D-glucopyranoside, 200 picomol p21 H-ras, 4.5 picomol [³H]FPP (activity 61000 dpm/picomol).

Reaction is initiated by adding approximately 5 ng of human farnesyl transferase purified from THP1 cell cultures. After incubation for 20 minutes at 37° C. in a microtitration plate containing 96 1-cm³ wells per plate (Titer Plate®, Beckman), the reaction is stopped by adding 0.4 cm³ of 0.1% SDS in methanol at 0° C. The mixture is then treated with 0.4 cm³ of 30% trichloroacetic acid (TCA) in methanol. The plates are left in ice for 1 hour. The precipitated contents are then retained on Filtermat®, Pharmacia) glass fibre membranes with the filtration unit (Combi Cell Harvester®, Skatron), and rinsed with 6% trichloro-acetic acid in distilled water. The membranes are dried in a microwave oven, then impregnated with scintillation medium by melting of Meltilex® (Pharmacia) under hot air, and lastly counted in cpm in a β-Plate counter® (LKB). Each test is repeated 3 times.

The unit of activity is defined as 1 picomole of [³H]FPP transferred to p21 H-Ras in 20 minutes.

The percentage inhibition values are obtained by comparison of the tests with and without inhibitor after deduction of blanks, the $IC_{50}$ values being measured on the basis of the inhibitions obtained with 9 different concentrations using Enzfitter® or Grafit® software.

The activity against cells can be determined in the following way:

The cell line is the THAC line (CCL 39 cells transfected with activated Ha-Ras) according to K. Seuwen et al., EMBO J., 7(1) 161–168 (1983). The cells are cultured in Petri dishes with a diameter of 6 cm containing a DMEM medium, 5% foetal calf serum and 1% G418.

After culturing for 24 hours, the culture medium is changed (with or without the serum) and the product to be studied is added in solution in dimethylformamide (DMF), in the presence or in the absence of DTT (final concentrations of 0.5% in DMF and 0.1 mM in DTT). After culturing for 24 hours at 37° C., the cells are lysed in 1 cm³ of lysis buffer (20 mM Tris, HCl, 1% Triton X114, 5 mM $MgCl_2$, 7 mM DTT, 150 mM NaCl, pH=7.4). The lysates are clarified by centrifuging at 4000 revolutions/minute for 10 minutes. Extraction with Triton X114 makes it possible to separate the farnesylated Ras protein from the non-farnesylated Ras protein (C. Bordier, J. Biol. Chem., 256 (4), 1604–1607 (1981)]. The farnesylated Ras protein, which is more hydrophobic, is found in the detergent phase whereas the non-farnesylated Ras protein is in the aqueous phase. The samples are denatured by heating at 95° C. in the denaturation buffer for electrophoresis and deposited on a 14% polyacryl-amide gel. When the dye reaches the bottom of the gel, the proteins of the gel are transferred onto a PVDF membrane. The Ras protein is visualized by the Western blot technique: the membrane is incubated with an anti-Ras specific monoclonal antibody (pan-Ras Ab3, Oncogène Science) and then with protein A labelled with 125I. After autoradiography, the bands are identified, cut out and counted in a γ counter. The radioactivity of the bands corresponding to farnesylated Ras and to non-farnesylated Ras makes it possible to determine the percentage of inhibition of farnesylation of the Ras protein.

The results obtained are collated in Table I.

TABLE I

| PRODUCT | Inhibitory activity $IC_{50}$ | % of inhibition against cells (THAC) |
|---|---|---|
| Example 1 | 48 | |
| Example 3 | 5.6 | |
| Example 5 | 69 | |
| Example 8 | 100 | |
| Example 9 | 70 | |
| Example 10 | 21 | |
| Example 19 | 1.8 | 31 to 50 µM |
| Example 20 | 80 | 50 to 10 µM |
| Example 21 | 4 nM | |

The new products of general formula (I) can be in the form of non-toxic and pharmaceutically acceptable salts. These non-toxic salts comprise the salts with inorganic acids (hydrochloric, sulphuric, hydrobromic, phosphoric and nitric acids) or with organic acids (acetic, trifluoroacetic, propionic, succinic, maleic, hydroxymaleic, benzoic, fumaric, methanesulphonic or oxalic acids), or with inorganic bases (sodium hydroxide, potassium hydroxide, lithium hydroxide, calcium hydroxide) or organic bases (tertiary amines such as triethylamine, piperidine, benzylamine), depending on the nature of the $R_1$ and $R_2$ symbols of the product of general formula (I).

The present invention also relates to pharmaceutical compositions containing at least one product of general formula (I), in combination with one or more pharmaceutically acceptable diluents or adjuvants, which may be either inert or physiologically active.

These compositions may be administered orally, parenterally or rectally.

The compositions for oral administration comprise tablets, pills, powders or granules. In these compositions, the active product according to the invention is mixed with one or more inert diluents such as sucrose, lactose or starch. These compositions can comprise substances other than diluents, for example lubricants such as magnesium stearate.

As liquid compositions for oral administration, solutions, suspensions, syrups, elixirs and pharmaceutically acceptable emulsions, containing inert diluents such as water or liquid paraffin, may be used. These compositions can also comprise substances other than diluents, for example wetting, sweetening or flavouring products.

The compositions according to the invention for parenteral administration can be sterile solutions, aqueous or non-aqueous, suspensions or emulsions. As solvent or vehicle, propylene glycol, a polyethylene glycol, vegetable oils, especially olive oil, or injectable organic esters, for example ethyl oleate, may be employed. These compositions can also contain adjuvants, especially wetting, emulsifying and dispersing agents. The sterilization may be carried out in several ways, for example using a bacteriological filter, by incorporating sterilizing agents in the composition or by heating. They may also be prepared in the form of sterile solid compositions which can be dissolved at the time of use in sterile water or any other sterile injectable medium.

The compositions for rectal administration are suppositories which can contain, besides the active product, excipients such as cocoa butter.

The compositions according to the invention are especially useful in human therapy in the treatment of cancers of various origins.

In human therapy, the doses depend on the effect sought, the period of treatment and factors specific to the subject to be treated.

Generally, in man, the doses are between 0.1 and 20 mg/kg per day via the intraperitoneal route.

A composition according to the invention is illustrated in the following example.

EXAMPLE 200 mg of the product obtained in Example 1 are dissolved in 100 cm³ of physiological serum. The solution obtained is divided up aseptically into 10 cm³ phials.

The phials are administered as a single injection or by perfusion.

We claim:

1. A compound of the formula (I):

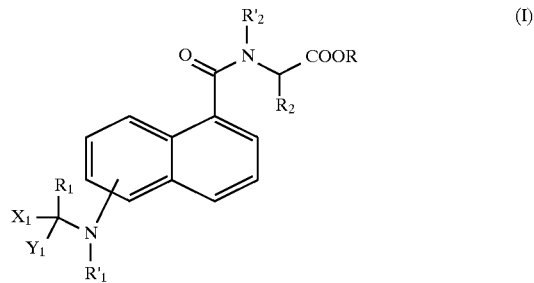

$R_1$ represents a radical of the formula Y—S—$A_1$— in which Y represents a hydrogen atom, an amino acid residue, a fatty acid residue, an alkyl radical, an alkoxycarbonyl radical, or an $R_4$—S— radical in which $R_4$ represents an alkyl radical comprising 1 to 4 carbon atoms, unsubstituted or substituted by a phenyl radical, or a radical of the formula (II):

(II)

wherein:
$A_1$ represents a straight or branched alkylene radical comprising 1 to 4 carbon atoms, unsubstituted or substituted at the position a to the >C($X_1$)($Y_1$) group by an amino radical, an alkylamino radical comprising 1 to 6 straight- or branched-chain Carbon atoms, a dialkylamino radical in which each alkyl portions comprises 1 to 6 straight- or branched-chain carbon atoms, an alkanoylamino radical comprising 1 to 6 straight- or branched-chain carbon atoms, or an alkoxycarbonylamino radical in which the alkyl portions comprises 1 to 6 straight- or branched-chain carbon atoms;

$X_1$ and $Y_1$ each represent a hydrogen atom or form, together with the carbon atom to which they are bonded, a >C=O group;

R'₁ represents a hydrogen atom or a methyl radical;

R₂ represents a straight or branched alkyl, alkenyl or alkynyl radical comprising 1 to 6 carbon atoms, unsubstituted or substituted by a hydroxyl radical, an alkoxy radical comprising 1 to 4 carbon atoms, a mercapto radical, an alkylthio radical comprising 1 to 4 carbon atoms, an alkylsulphinyl radical comprising 1 to 4 carbon atoms, or an alkylsulphonyl radical comprising 1 to 4 carbon atoms, wherein when R₂ represents an alkyl radical substituted by a hydroxyl radical, R₂ can form a lactone with the carboxyl radical at the α position;

R'₂ represents a hydrogen atom or a methyl radical; and

R represents a hydrogen atom or an alkyl radical comprising 1 to 6 carbon atoms, unsubstituted or substituted by an alkoxy radical comprising 1 to 4 carbon atoms, an alkylthio radical comprising 1 to 4 carbon atoms, an alkylsulphinyl radical comprising 1 to 4 carbon atoms, an alkylsulphonyl radical comprising 1 to 4 carbon atoms, a phenyl radical, a phenoxy radical, a phenylthio radical, a phenylsulphinyl radical, a phenylsulphonyl radical, an alkylamino radical comprising 1 to 4 carbon atoms, a dialkylamino radical in which each alkyl portion comprises 1 to 4 carbon atoms, or a phenyl radical, unsubstituted or substituted by at least one substituent selected from the group consisting of a halogen atom, an alkyl radical, an alkyloxy radical, an alkylthio radical, and an alkanoyl radical;

wherein the radical

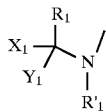

is in the 5- or 6-position of the naphthyl ring.

2. The compound according to claim 1, wherein:

R₁ represents a radical of formula Y—S—A₁— in which Y represents a hydrogen atom, a lysine residue, a fatty acid residue comprising up to 20 carbon atoms, and A₁ represents an ethylene or propylene radical unsubstituted or substituted by an amino radical or alkylamino radical comprising 1 to 4 carbon atoms;

X₁ and Y₁ each represent a hydrogen atom or form, together with the carbon atom to which they are bonded, a >C=O group;

R'₁ represents a hydrogen atom or a methyl radical;

R₂ represents an alkyl radical comprising 1 to 4 carbon atoms, unsubstituted or substituted by a hydroxyl, methoxy, mercapto, methylthio, methylsulphinyl, or methylsulphonyl radical;

R'₂ represents a hydrogen atom or a methyl radical; and

R represents a hydrogen atom or an alkyl radical comprising 1 to 4 carbon atoms, unsubstituted or substituted by an alkoxy radical or a phenyl radical.

3. The compound according to claim 1, wherein:

R₁ represents a radical of formula Y—S—A₁— in which Y represents a hydrogen atom and A₁ represents an ethylene or propylene radical unsubstituted or substituted by an amino radical;

X₁ and Y₁ each represent a hydrogen atom or form, together with the carbon atom to which they are bonded, a >C=O group;

R'₁ represents a hydrogen atom;

R₂ represents a methyl, ethyl, propyl or butyl radical unsubstituted or substituted by a hydroxyl, methoxy, mercapto or methylthio radical;

R'₂ represents a hydrogen atom; and

R represents a hydrogen atom or an alkyl radical comprising 1 to 4 carbon atoms.

4. The compound according to claim 1, wherein:

R₁ represents a 2-mercaptoethyl or 1-amino-2-mercaptoethyl radical;

X₁ and Y₁ each represent a hydrogen atom or form, together with the carbon atom to which they are bonded, a >C=O group;

R'₁ represents a hydrogen atom;

R₂ represents an n-butyl or 2-(methylthio)ethyl radical;

R'₂ represents a hydrogen atom; and

R represents a hydrogen atom or a methyl radical.

5. A pharmaceutical composition comprising a compound according to claim 1 and at least one pharmaceutically acceptable carrier.

* * * * *

UNITED STATES PATENT AND TRADEMARK OFFICE
CERTIFICATE OF CORRECTION

PATENT NO. : 5,861,529
DATED : January 19, 1999
INVENTOR(S) : Baudoin et al.

It is certified that error appears in the above-identified patent and that said Letters Patent is hereby corrected as shown below:

On the Title Page, Item [75], in the inventors, line 3, "Commercon" should read --Commerçon--

On the Title Page, Item [57], in the Abstract, line 12, "position a " should read --position α--.

Claim 1, column 30, line 34, before "R, represents", insert the line --wherein:--.

Claim 1, column 30, line 56, "position a " should read --position α--.

Claim 1, column 30, line 58, "Carbon" should read --carbon--.

Signed and Sealed this

Second Day of November, 1999

Attest:

Attesting Officer

Q. TODD DICKINSON

Acting Commissioner of Patents and Trademarks